US007846190B2

(12) United States Patent
Ball

(10) Patent No.: US 7,846,190 B2
(45) Date of Patent: *Dec. 7, 2010

(54) APPARATUSES, SYSTEMS AND METHODS FOR BONE FIXATION

(75) Inventor: Robert J. Ball, San Marcos, CA (US)

(73) Assignee: Integra Lifesciences Corporation, Plainsboro, NJ (US)

(*) Notice: Subject to any disclaimer, the term of this patent is extended or adjusted under 35 U.S.C. 154(b) by 1231 days.

This patent is subject to a terminal disclaimer.

(21) Appl. No.: 11/010,825

(22) Filed: Dec. 13, 2004

(65) Prior Publication Data

US 2005/0251137 A1   Nov. 10, 2005

Related U.S. Application Data

(60) Provisional application No. 60/529,392, filed on Dec. 12, 2003.

(51) Int. Cl.
    *A61B 17/04* (2006.01)
    *A61F 2/08* (2006.01)
(52) U.S. Cl. ..................................... 606/313
(58) Field of Classification Search ......... 606/300–306, 606/313, 314, 319, 280, 281, 286, 287, 288, 606/289, 290, 295, 297
    See application file for complete search history.

(56) References Cited

U.S. PATENT DOCUMENTS 1,025,275 A * 5/1912 Kennedy ..................... 411/63

(Continued)

FOREIGN PATENT DOCUMENTS

WO   WO88/03781   6/1988

(Continued)

OTHER PUBLICATIONS

European Patent Office Supplementary Partial European Search Report dated Nov. 13, 2008.

(Continued)

*Primary Examiner*—Anu Ramana
(74) *Attorney, Agent, or Firm*—Jenkins, Wilson, Taylor & Hunt, P.A.

(57) ABSTRACT

Apparatuses, systems and methods for bone fixation are disclosed herein. A fixation apparatus is disclosed having a head portion having outer wall sections at least partially surrounding a central hollow area, and the head portion also having an inner bottom surface. A shank portion can extend from the head portion. An expander hub is provided for positioning at least partially within the central hollow area of the head portion and can be seated at least partially on the inner bottom surface of the head portion. The expander hub is rotatable to force the outer wall sections of the head portion outwardly for engaging and locking the fixation apparatus in place when the fixation apparatus is positioned within a hole of a plate. The fixation apparatus can advantageously be used with a plate whereby the fixation apparatus and plate can compress bone separately from locking the fixation apparatus in a desired position. Also, the angle, alignment or position of the fixation apparatus can be changed if desired even after locking of the fixation apparatus. Separate drivers can be used to drive the fixation apparatus, to rotate the expander hub to lock it in place, and to remove the fixation apparatus. The drivers can be cannulated as desired such that the drivers can be assembled in a nested and concentric configuration and can be used without removal from the nested configuration.

40 Claims, 20 Drawing Sheets

U.S. PATENT DOCUMENTS

| | | | |
|---|---|---|---|
| 4,026,187 A * | 5/1977 | Gross | 411/41 |
| 5,683,390 A * | 11/1997 | Metz-Stavenhagen et al. | 606/278 |
| 5,954,722 A | 9/1999 | Bono | |
| 5,957,953 A * | 9/1999 | DiPoto et al. | 606/232 |
| 6,022,352 A | 2/2000 | Vandewalle | |
| 6,030,389 A * | 2/2000 | Wagner et al. | 606/71 |
| 6,117,173 A * | 9/2000 | Taddia et al. | 623/16.11 |
| 6,413,259 B1 | 7/2002 | Lyons et al. | |
| 6,440,135 B2 | 8/2002 | Orbay et al. | |
| 6,540,746 B1 | 4/2003 | Bühler et al. | |
| 6,554,834 B1 | 4/2003 | Crozet et al. | |
| 6,716,214 B1 | 4/2004 | Jackson | |
| 7,063,701 B2 * | 6/2006 | Michelson | 606/307 |
| 7,163,538 B2 * | 1/2007 | Altarac et al. | 606/86 A |
| 2003/0199876 A1 | 10/2003 | Brace et al. | |
| 2003/0199983 A1 | 10/2003 | Michelson | |

FOREIGN PATENT DOCUMENTS

| | | |
|---|---|---|
| WO | WO94/26193 | 11/1994 |
| WO | WO97/22306 | 6/1997 |
| WO | WO02/22030 A2 | 3/2002 |
| WO | WO2004/039236 A2 | 5/2004 |

OTHER PUBLICATIONS

International Search Report for PCT/US04/41590 dated Dec. 22, 2005.

International Preliminary Report of Patentability for PCT/US2004/041590 dated Jun. 22, 2006.

Notice of Allowance for U.S. Appl. No. 11/292,333 dated Dec. 16, 2009.

* cited by examiner

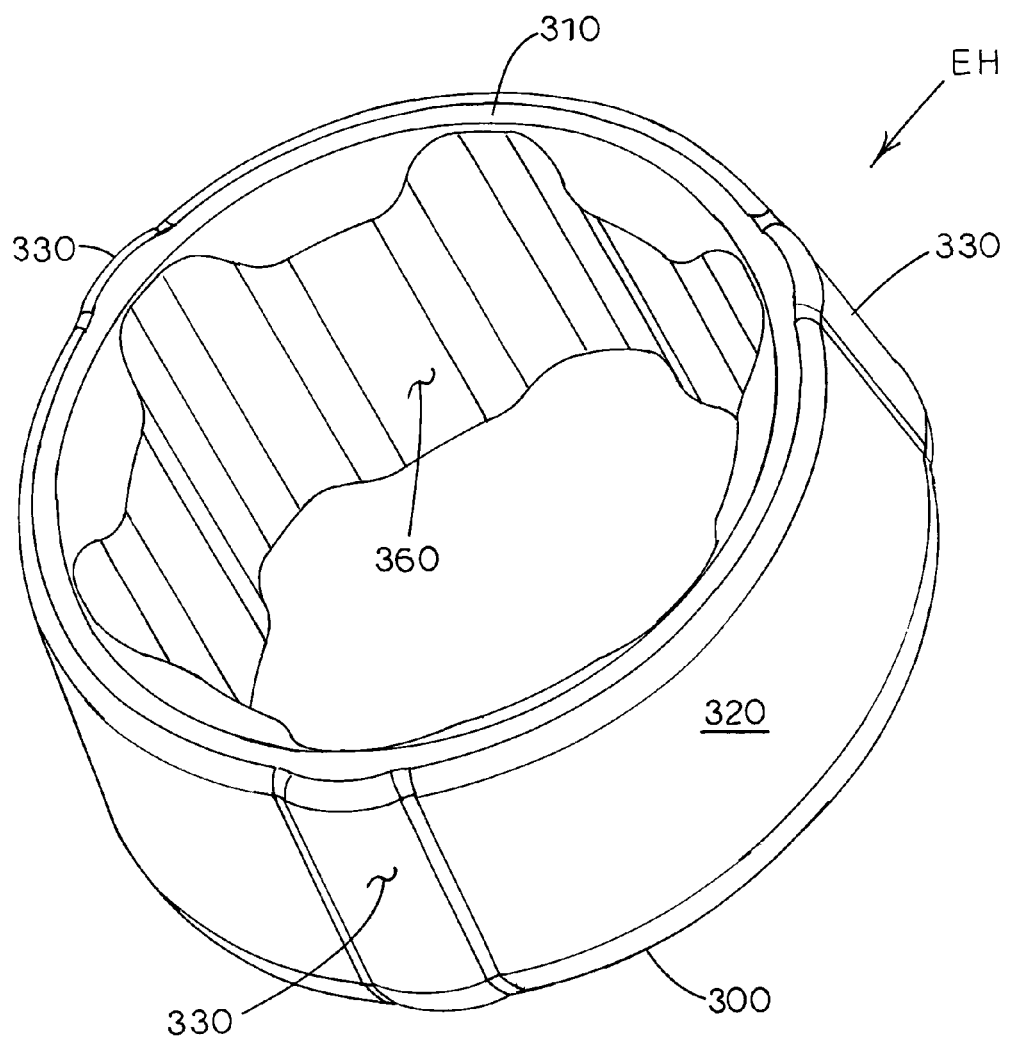
Fig · 5A

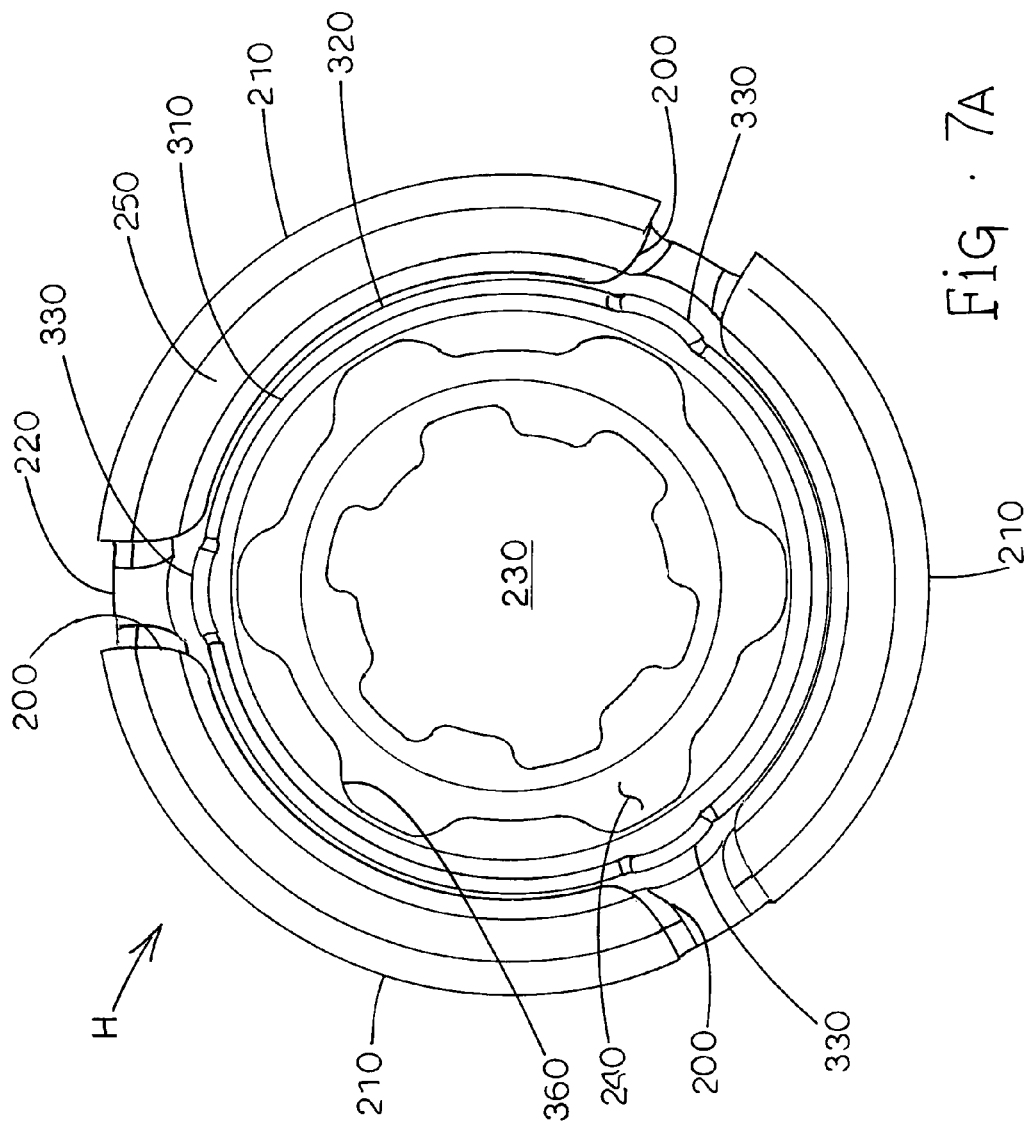

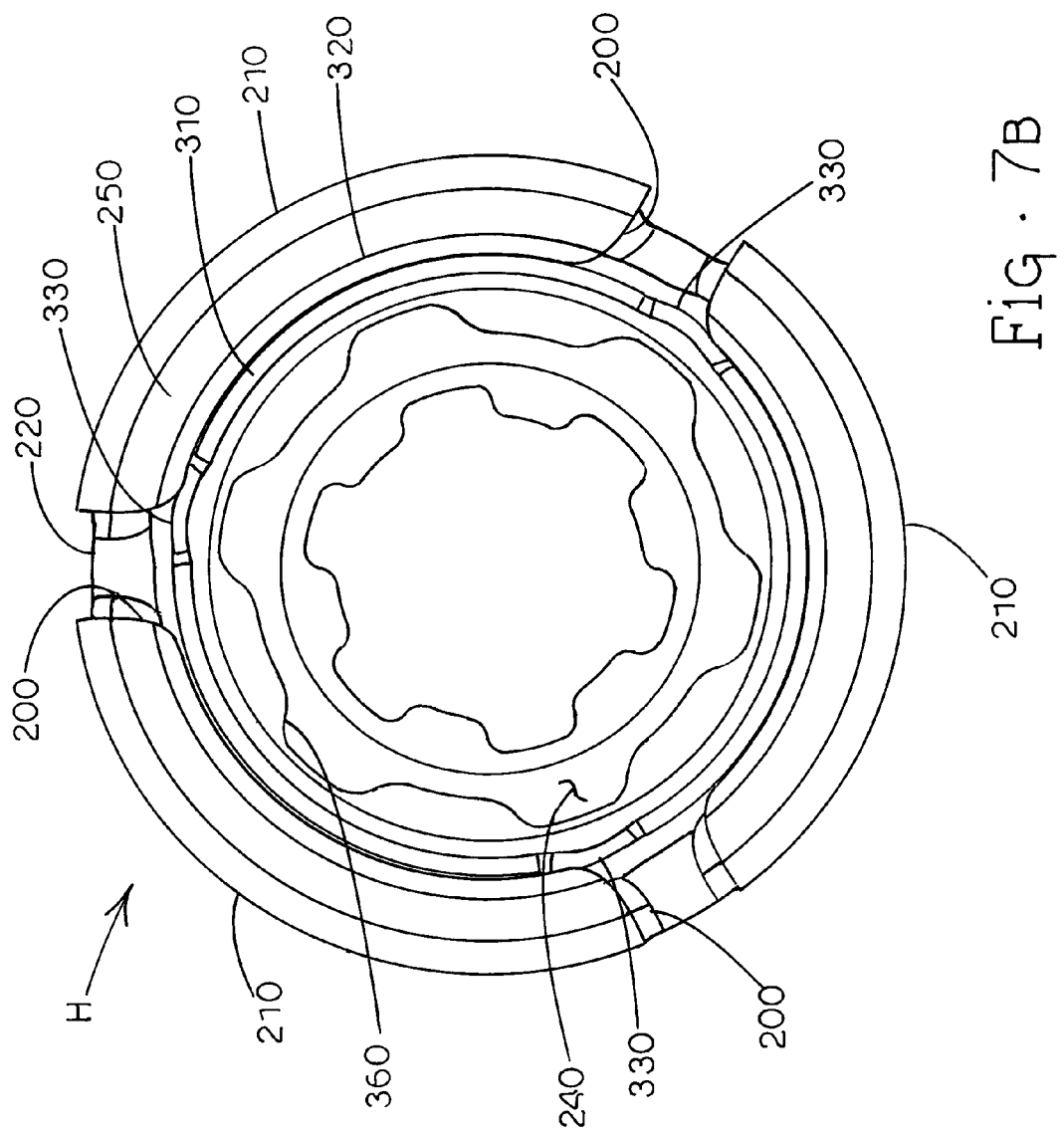

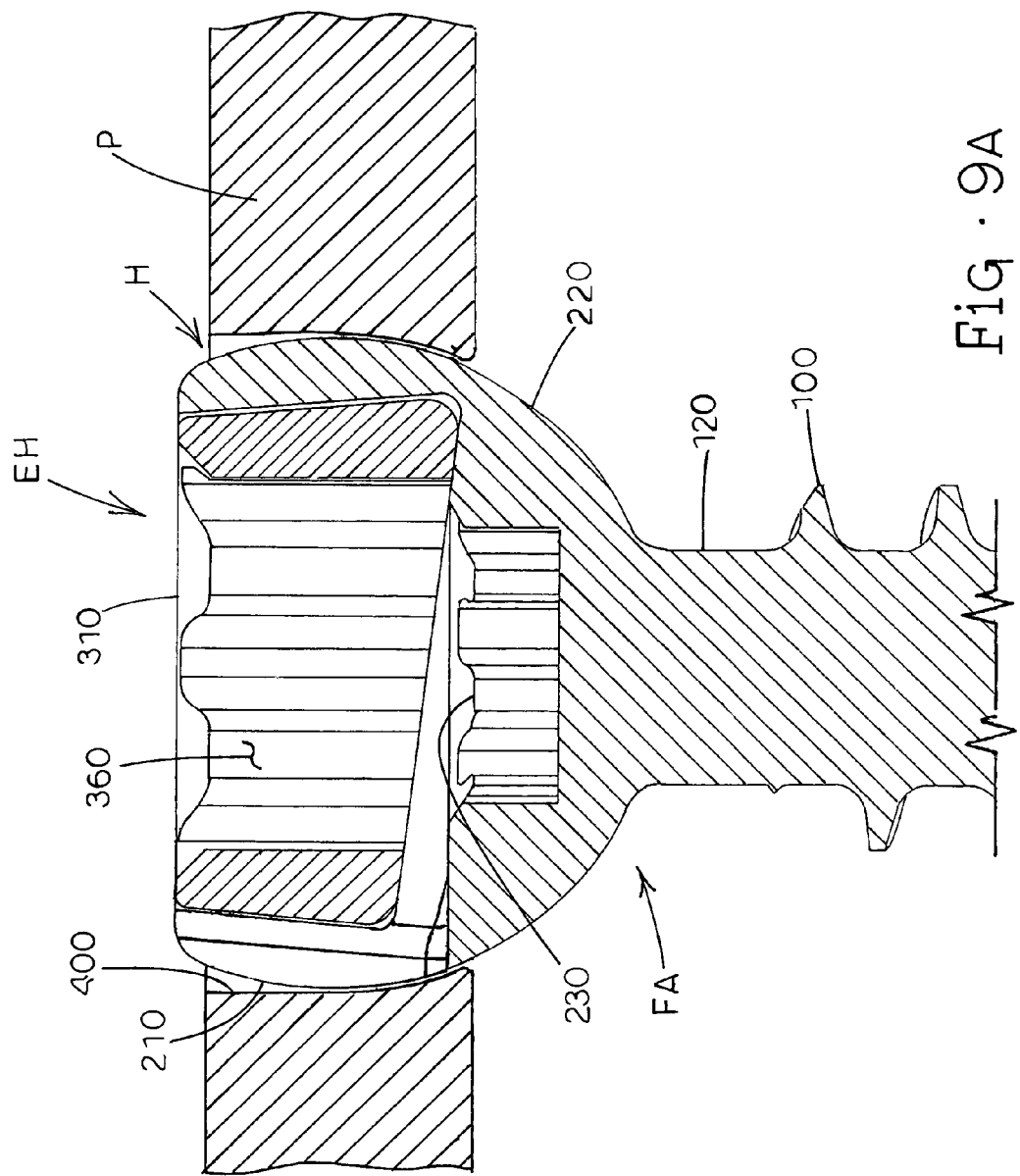

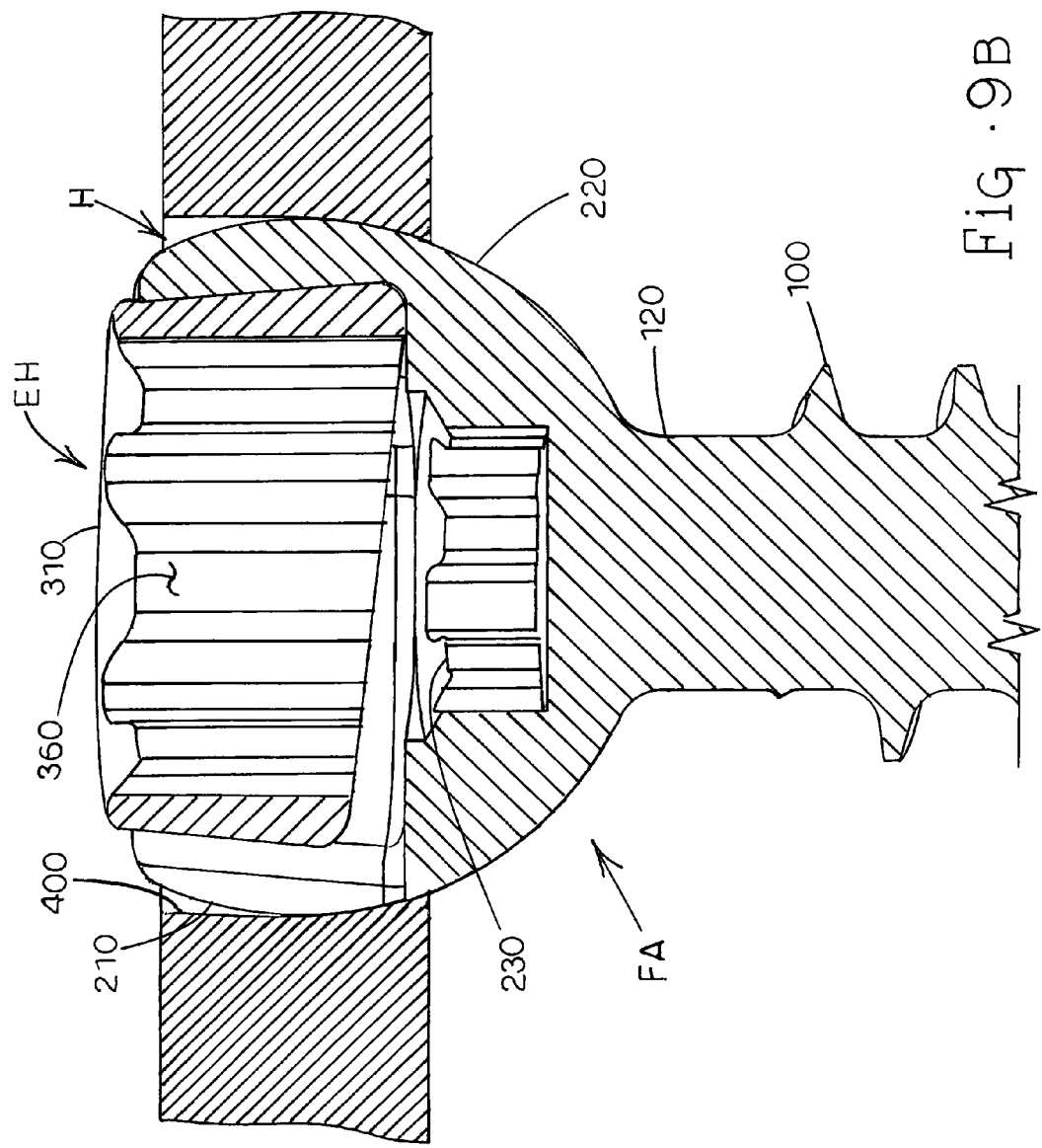

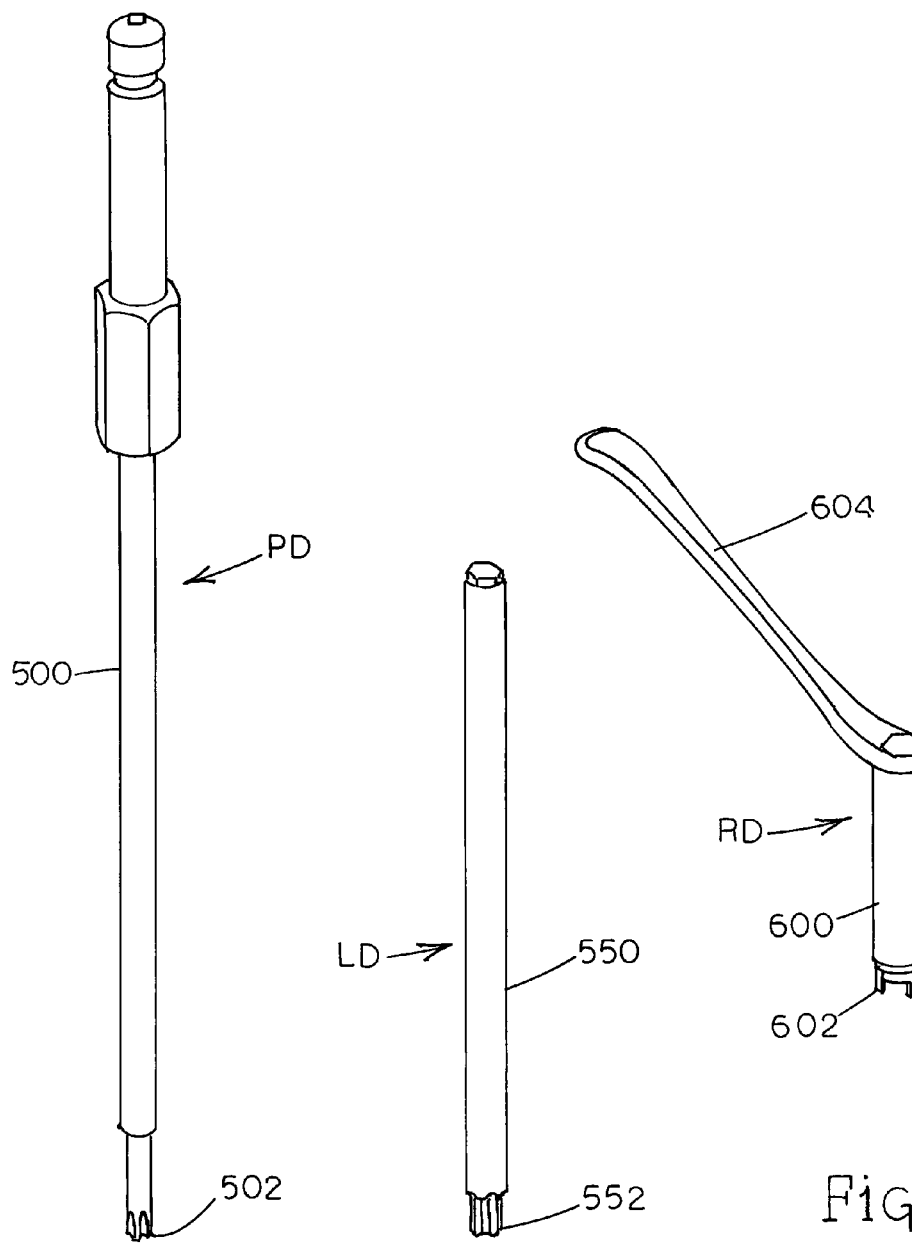

APPARATUSES, SYSTEMS AND METHODS FOR BONE FIXATION

RELATED APPLICATIONS

This application claims the benefit of U.S. Provisional Patent Application Ser. No. 60/529,392, filed Dec. 12, 2003, the disclosure of which is incorporated herein by reference in its entirety.

TECHNICAL FIELD

The present subject matter relates generally to bone fixation and, more particularly to apparatuses, systems and methods for bone fixation utilizing a fixation apparatus to lock in various locked positions in order to fixate bone.

BACKGROUND ART

A variety of apparatuses and methods are known in the field of orthopedics for reducing, fixing and generally assisting the healing of fractured bones. In some cases, these apparatuses and methods require surgical intervention. Open reduction internal fixation (ORIF) is a developed art with respect to some portions of the body; however, many complications can exist which can prevent successful or optimal outcomes in all cases utilizing ORIF. Treatment methods can also significantly impact healing time, pain and functional outcomes. Moreover, the necessity of reducing operative time is driven both by patient risk of infection, and aesthetic complications, and health care costs. Thus, efforts continue to be made to improve fixation devices and surgical techniques in an attempt to improve surgical outcomes, costs and operative times.

Several factors are considered to be well known which can have significant impact in predicting outcomes of ORIF. These factors include:

1. Prominence of hardware, leading to soft tissue abrasion and general inflammation.
2. Accurate reduction of fracture site providing proper alignment in all degrees of freedom.
3. Reliable fixation that rigidly approximates bone segments during healing.
4. Production of adequate and predictable compression across fracture sites which provides impetus for improved healing.
5. Minimization of skin incision and exposure to patient.
6. Reduced operative times.

Thus, it is desirable to utilize a fracture fixation apparatus and method which provides for low-profile hardware, or hardware countersunk into bone, which reduces or eliminates soft tissue abrasions and inflammation. Additionally, it is desirable to utilize an apparatus and method that provides for reproducible reduction, fixation, and also accurate bone compression to optimize the healing process. Such an apparatus and method must also minimize skin incision and provide a method that is simple and timely in terms of operating room resources and patient risk. Since fractures can occur in all bones of the body, both large and small, it is further desirable to utilize a consistent apparatus and method that can be used and scaled to fit all size applications regardless of the size of a bone fracture.

Fixation plates are common apparatuses used in orthopedic surgery for fixing two or more bone fragments together. Commonly, a plate with several holes defined in the plate is placed adjacent to bone fragments, and screws are driven through the plate holes and into the bone fragments. This method can often provide a satisfactory reduction and fixation where sufficient bony material is available for firmly grasping and orienting a screw/plate construct. More specifically, when a fixation apparatus is able to penetrate and engage two bone cortices, the fixation apparatus is firmly supported in two locations and will thus be rotationally aligned with the plate. If the fixation apparatus is, however, only able to grasp one cortice, and in a normal case, the proximal cortice, rotational alignment is not firmly engaged between the fixation apparatus and the plate and accurate reduction of the fixation site may not be maintained. This problem is also common in the areas of the body not involving particularly long bones, such as the hand, foot and spine. This problem also commonly exists in unhealthy (rheumatoid or osteoporotic) bone that simply cannot purchase bone as firmly as healthy bone.

A variety of apparatuses and methods have existed and exist in the prior art relating to bone fracture repair. The first generation of designs for screw/plate hardware used in fracture repair consisted of simply designed mechanisms using conventional hardware and materials compatible with the application. There was little effort to reduce the profile to protect soft tissue or control the position. The second generation added to the technology of the first generation by simply making allowance for the screw to sit into the profile of the plate (countersunk) so that soft tissue abrasion was minimized.

The third generation utilized a spherical countersunk screw in plate design as it became evident as plates were used more widely through the body that it was desirable to allow the screw to be positioned in many or a range or angles relative to the plate. By creating a sphere and globular socket mechanism, a solid construct could be obtained with the screw at any angle to the plate. The fact that the screw can engage two cortices allowed the angle to be fixed. The fourth generation utilized a fixed angle countersunk screw in plate design as screw and plate mechanisms were continually used in smaller and more complex regions of the body. There was a need to be able to hold bony structures rigidly in situations where little inherent support was available. A fixed angle between the screw and plate was created by threading the head of the screw into the plate. The angle of the screw relative to the plate was determined at manufacture of the hardware. This technology is represented at least in part by U.S. Pat. No. 6,440,135 to Orbay et al.

One invention currently sold under the mark PEAK by DePuy Acromed (Raynham, Mass.) is disclosed in U.S. Pat. No. 5,954,722 to Bono. The apparatus described in this patent utilizes a plate with holes which have spherical diameter bores into which fit spherical outer diameter bushings. The bushings have a tapered, threaded inner diameter, and a specially designed screw is available that has a tapered head matching that of the bushing. As the screw is driven through the bushing, the threads engage and produce a radial force in the bushing, pushing against the inner wall of the plate. The alignment of the screw to the plate is held with a moment corresponding to the amount of friction between the bushing and the plate. Primary shortcomings of this apparatus include:

1. The angle of the screw must be determined prior to insertion of the screw.
2. The screw cannot optionally be allowed to remain unlocked as a locking construct must be used.
3. The locking mechanism requires careful planning upon insertion as long as there is propensity for "cross-threading" the construct due to its fine thread and long length.
4. Compression of bone with the screw independent of locking the screw in place is either not possible or is limited.

SUMMARY

Apparatuses, systems and methods for bone fixation are disclosed herein. A fixation apparatus according to the subject matter disclosed herein can comprise a head portion that can include a plurality of outer wall sections at least partially surrounding a central hollow area. The head portion also has an inner bottom surface. An expander hub is provided for positioning at least partially within the central hollow area and can be seated at least partially on the inner bottom surface of the head portion. The expander hub is rotatable to force the outer wall sections of the head portion outwardly for locking the fixation apparatus in place when the fixation apparatus is positioned within a hole of a plate for fixating a bone fracture. A shank portion can optionally extend from the head portion for engaging bone as described further hereinbelow. The fixation apparatus can advantageously be used with a plate whereby the fixation apparatus and plate can compress bone separately from locking the fixation apparatus in a desired position. Also, the angle, alignment or position of the fixation apparatus can be changed if desired even after locking of the fixation apparatus. Separate drivers can be used to drive the fixation apparatus, to rotate the expander hub to lock it in place, and to limit rotation of the head during locking, if necessary. The drivers can be cannulated as desired such that the drivers can be assembled in a nested configuration and can be used without removal from the nested configuration.

It is therefore an object to provide novel systems, apparatuses and methods for bone fixation. This and other objects as may become apparent from the present disclosure are achieved, in whole or in part, by the subject matter disclosed herein.

BRIEF DESCRIPTION OF THE DRAWINGS

FIG. 5A of the drawings is a perspective view of the expander hub shown in FIG. 1;

FIG. 7A-7C of the drawings are end views of the head portion of the fixation apparatus shown in FIG. 6 illustrating various positions of the expander hub;

FIG. 9A of the drawings is a sectional view illustrating a portion of the fixation apparatus with the expander hub in an unlocked position;

FIG. 9B of the drawings is a sectional view illustrating a portion of the fixation apparatus with the expander hub in a locked position;

FIGS. 11A-11C of the drawings are perspective views of drivers that can be used in association with the fixation apparatus shown in the previous figures;

DETAILED DESCRIPTION

In accordance with the subject matter disclosed herein, and with reference to the various figures of drawings, apparatuses, systems and methods are provided for fixating a fractured bone with the ability to establish and maintain accurate alignment and reduction of bone fragments as well as to maintain such reduction through the healing process. As described in detail hereinbelow, a fixation apparatus in accordance with the present disclosure can be utilized in association with a plate in order to achieve and maintain desired alignment, independent of the level of fixation, in order to facilitate healing of a bone fracture.

Figure 1:
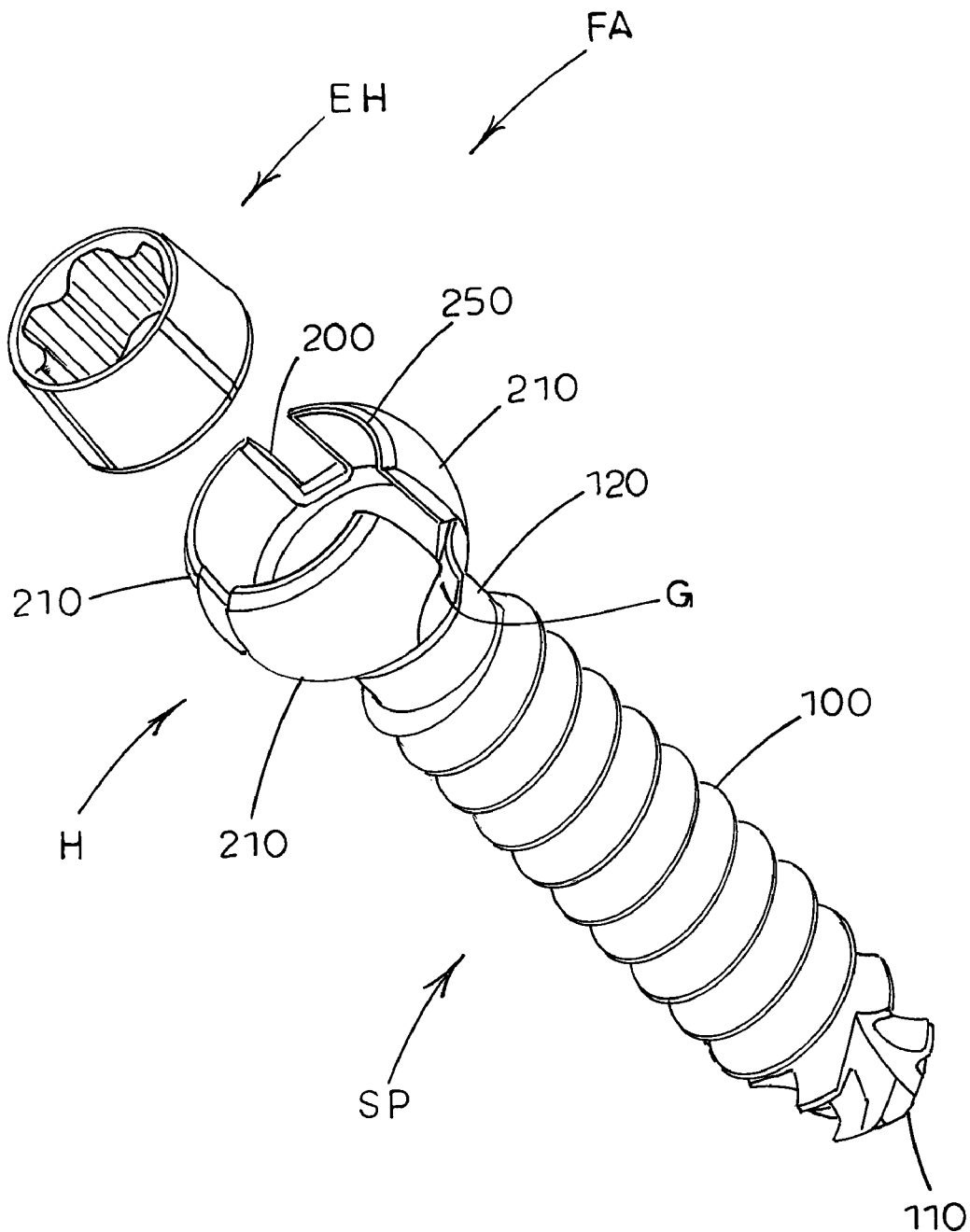
FIG. 1 of the drawings is a perspective view of an embodiment of a fixation apparatus with an expander hub shown detached.
Figure 2:
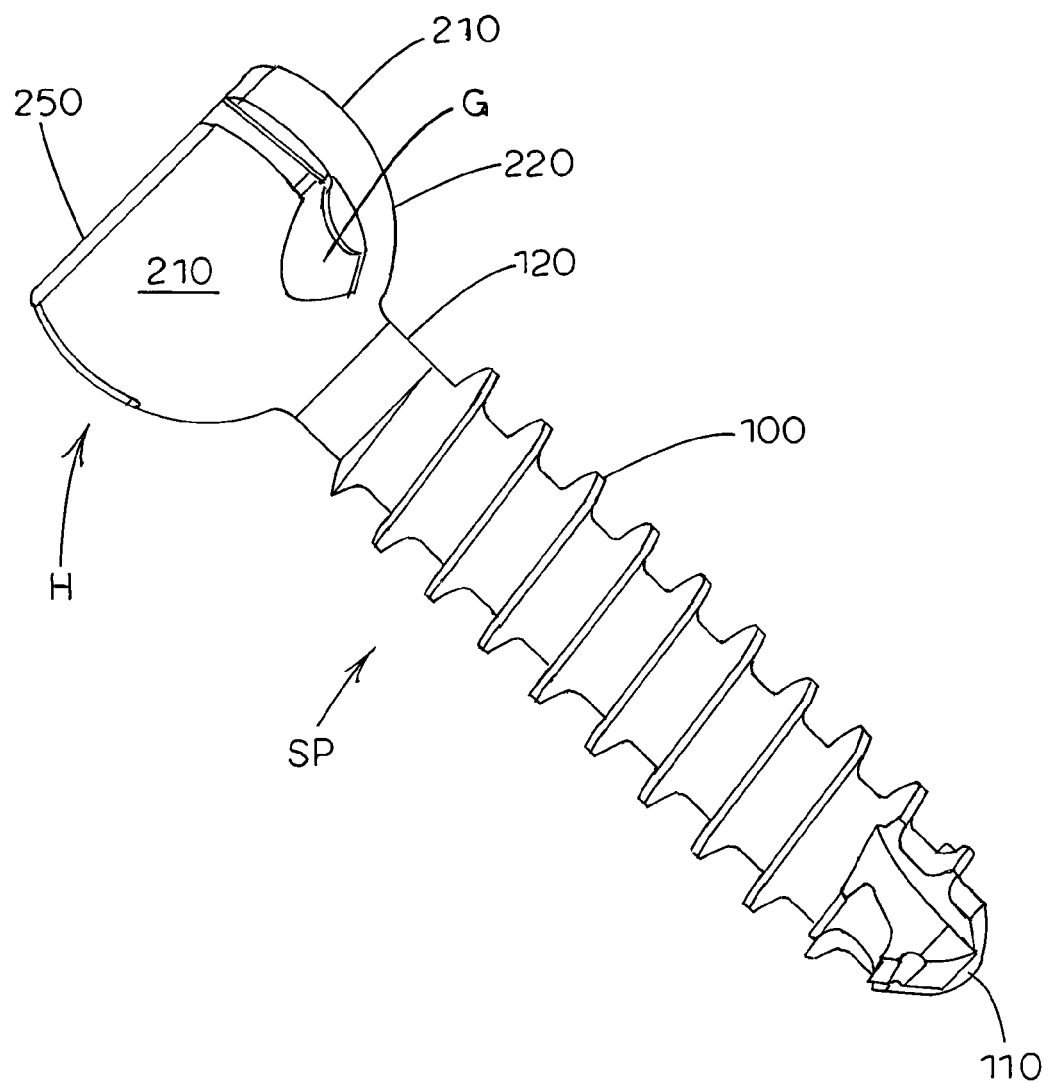
FIG. 2 of the drawings is a side view of the fixation apparatus shown in FIG. 1 without the expander hub.

Referring now to FIGS. 1 and 2 of the drawings, fixation apparatus generally designated FA is illustrated and comprises a head portion generally designated H which can have a shank portion generally designated SP extending therefrom. An expander hub generally designated EH is shown in FIG. 1 adapted for fitting into head portion H as described later in greater detail and as shown forth for illustration purposes in FIG. 1 detached from head portion H. As can be appreciated by those of skill in the art, shank portion SP can be formed as an integral part of and extension from head portion H or can separate and independent from head portion H.

Shank portion SP can be any suitable shank portion, threaded or unthreaded, and is illustrated in the drawings in one suitable, non-limiting configuration. As shown in FIGS. 1 and 2, a threaded shank portion SP of fixation apparatus FA can include any suitable type of thread, such as threads 100, along at least a portion of the length of shank portion SP and can also include a tip 110 which can be self-tapping, for facilitating screwing or otherwise placing fixation apparatus FA into bone. As can be appreciated by those of skill in the art, shank portion SP of fixation apparatus FA can be cannulated if desired and define an axial opening along the middle of shank portion SP Shank portion SP can be self-drilling and can be constructed of any suitable material known to those of skill in the art, such as, for example, titanium.

Head portion H of fixation apparatus FA can be integral with or separate from and attached to an end of shank portion SP opposite from the end of shank portion SP which includes tip 110. Head portion H can be of any suitable shape in accordance with the functionality described in the present disclosure and can be constructed of any suitable material known to those of skill in the art, such as, for example, titanium. One or more slots, such as slots 200 can be defined through portions of the wall of head portion H thereby creating wall sections 210 which are separated by slots 200 as illustrated, but that all extend from a base portion 220 of head portion H with base portion 220 being the part of head portion H closest to shank portion SP.

Expander hub EH of fixation apparatus FA can be of any suitable shape or configuration for functionality in accordance with the present disclosure as will be appreciated by those of skill in the art. As illustrated, expander hub EH is at least generally cylindrical in shape with a reverse, tapered outer diameter and an inclined, lower surface as described in greater detail hereinbelow. Expander hub EH can have a plurality of annular recesses and is adapted for fitting into a recessed portion of head portion H of fixation apparatus FA where it can be positioned in a disengaged or unlocked position wherein wall sections 210 of head portion H are not forced outwardly, and an engaged or locked position wherein wall sections 210 of head portion H are forced outwardly sufficient to lock fixation apparatus FA in a predetermined position as described further hereinbelow. As with the previous structures, expander hub EH can be constructed of any suitable material known to those of skill in the art, such as, for example, titanium.

As shown in FIGS. 1 and 2 (and FIG. 10 described below) of the drawings, head portion H can advantageously comprise a groove G that can be defined in the lower portion of head portion H and allows head portion H to be self-counterboring into bone. Screw heads with additional features, such as locking, can often be thicker than desired such that bone has to be countersunk to allow the screw head to sit in a thinner plate. This countersinking requires an additional step, therefore making the self-counterboring feature of head portion H quite advantageous.

Figure 3:
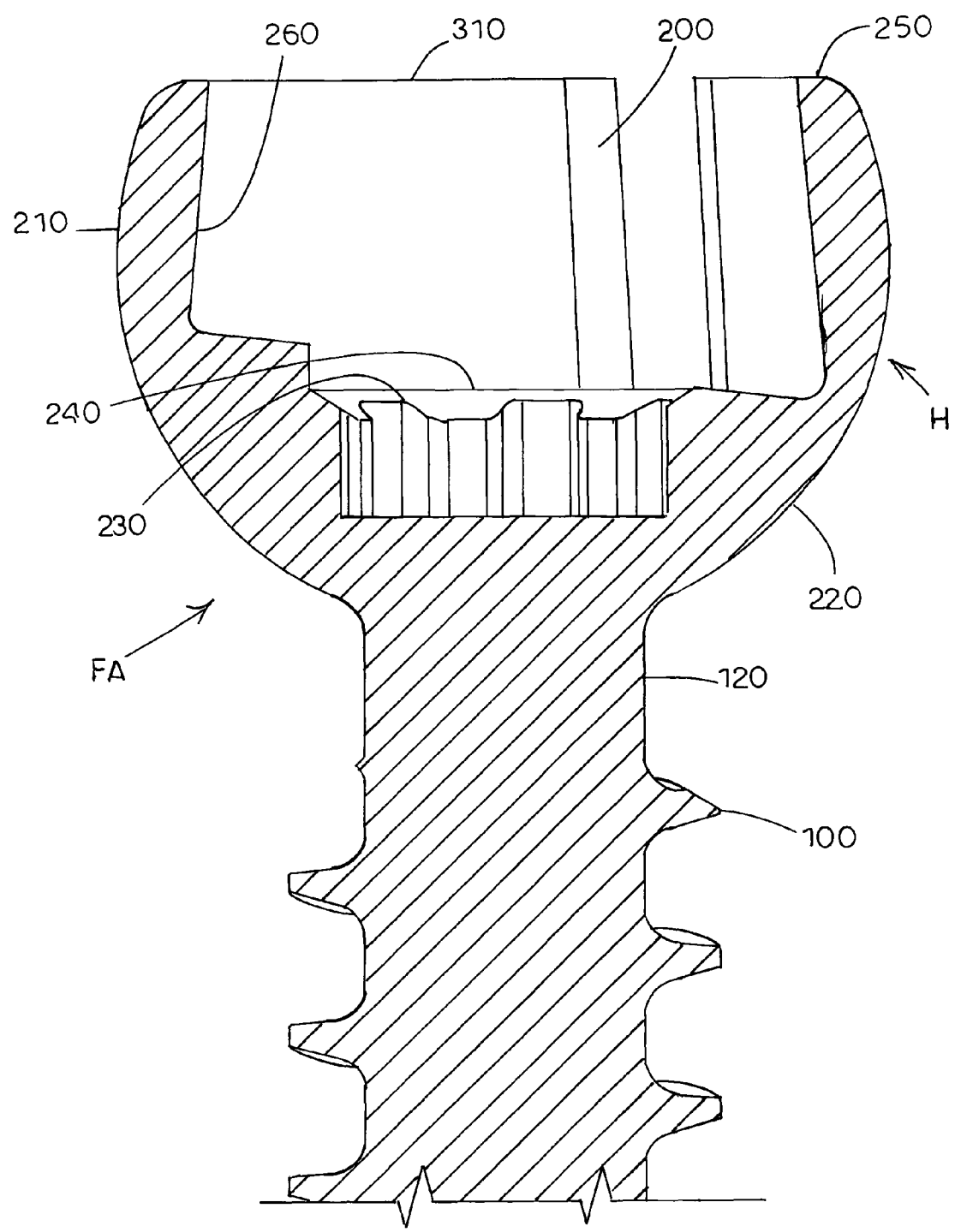
FIG. 3 of the drawings is a sectional view of an end portion of the fixation apparatus shown in FIG. 2.
Figure 4:
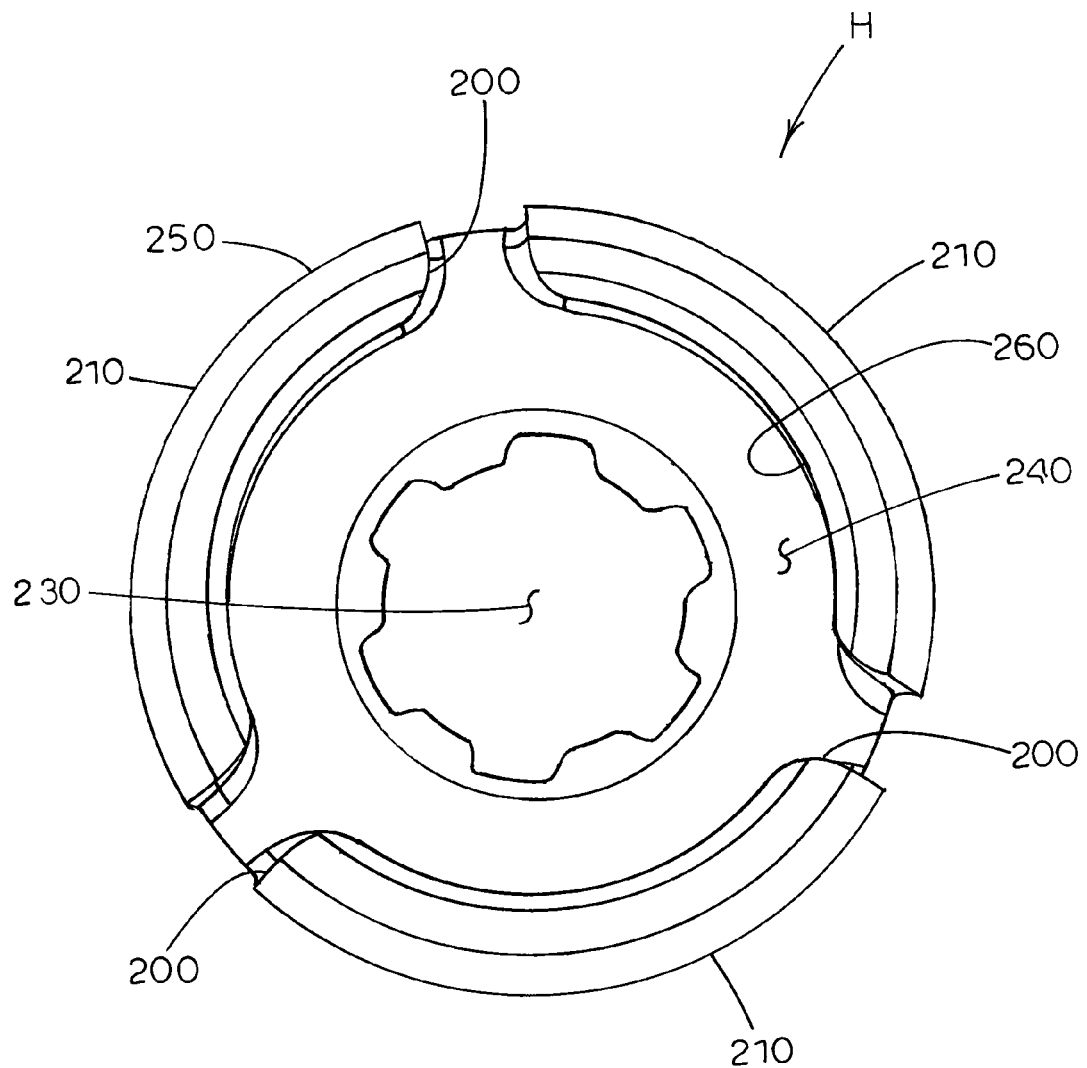
FIG. 4 of the drawings is an end view of the fixation apparatus shown in FIG. 2.

Referring now to FIG. 3 of the drawings, a cross-sectional view of head portion H and shank portion SP of fixation apparatus FA is illustrated. Expander hub EH is not present in FIG. 3. Shank portion SP can be of any suitable design with outer threads 100 adapted for screwing into bone. Head portion HP, however, advantageously comprises slot 200 wall sections 210 and base portion 220 as illustrated in FIG. 3 wherein base portion 220 includes a recess designated 230. Recess 230 is perhaps best illustrated in FIGS. 3 and 4 of the drawings and can be of any suitable shape or configuration adapted for receiving a driver in order to rotatably drive head portion H and shank portion SP when present and when desired such as when shank portion SP is threaded for screwing shank portion SP into bone. As shown in FIG. 4, recess 230 of base portion 220 defines a hexagonal configuration adapted to receive a suitably shaped driver with a matching hexagonal end for being matingly received into recess 230 for rotatably driving head portion H and shank portion SP.

Still referring to FIGS. 3 and 4 primarily, recess 230 of base portion 220 is advantageously defined in an upper surface 240 of base portion 220 of head portion H. Upper surface 240 is preferably slightly inclined from one side of head portion H to the other as illustrated in FIG. 3 to facilitate the locking feature of expander hub EH (shown in FIG. 1) when positioned in head portion H as described further hereinbelow. The hollow or recessed portion of head portion H at least partially surrounded by wall sections 210 can be of a larger diameter at the bottom thereof (at upper surface 240 of base portion 220) than at the top end 250 of head portion H. To achieve this feature, the inner portions or sides 260 of wall sections 210 facing the interior of head portion H can have a reverse taper and extend gradually further inwardly the further they extend from upper surface 240 of base portion 220. Slots 200 of head portion H as illustrated in FIG. 3 can be defined from top end 250 of head portion H to base portion 220 and extend along a line that is at least generally parallel to a longitudinal, central axis of shank portion SP. Groove G (shown in FIGS. 1 and 2) can be defined in the lower portion of head portion H below slots 200 of head portion H in order for head portion H to be self-counterboring into bone FIGS. 5A, 5B, 5C and 5D of the drawings illustrate expander hub EH which is adapted to fit into the recessed portion of head portion H at least partially surrounded by wall sections 210 above base portion 220. Expander hub EH can be at least generally cylindrical in shape and have a reverse tapered outer diameter such that the outer diameter of expander hub EH is greater at its bottom or lowest surface 300 than the outer diameter of expander hub EH at the opposite uppermost surface 310. Expander hub EH includes an outer wall 320 which can optionally comprise one or more lobes, such as lobes 330, three of which are shown on expander hub EH in the disclosed embodiments. Lobes 330 can be formed as expanded bands or portions of outer wall 320 and can be spaced-apart equally on outer wall 320.

Figure 5B:
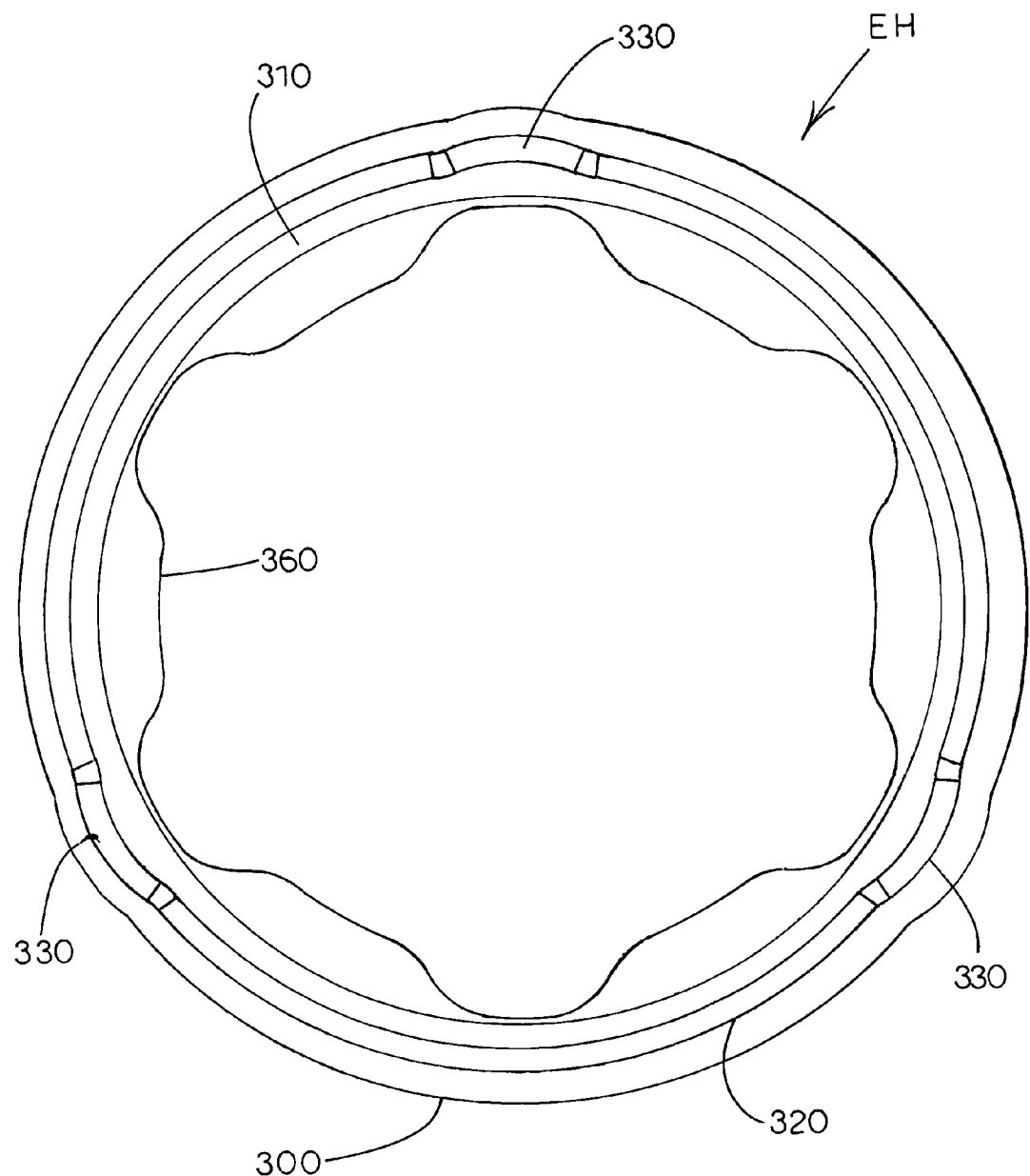
FIG. 5B of the drawings is a top plan view of the expander hub shown in FIG. 1.
Figure 5C:
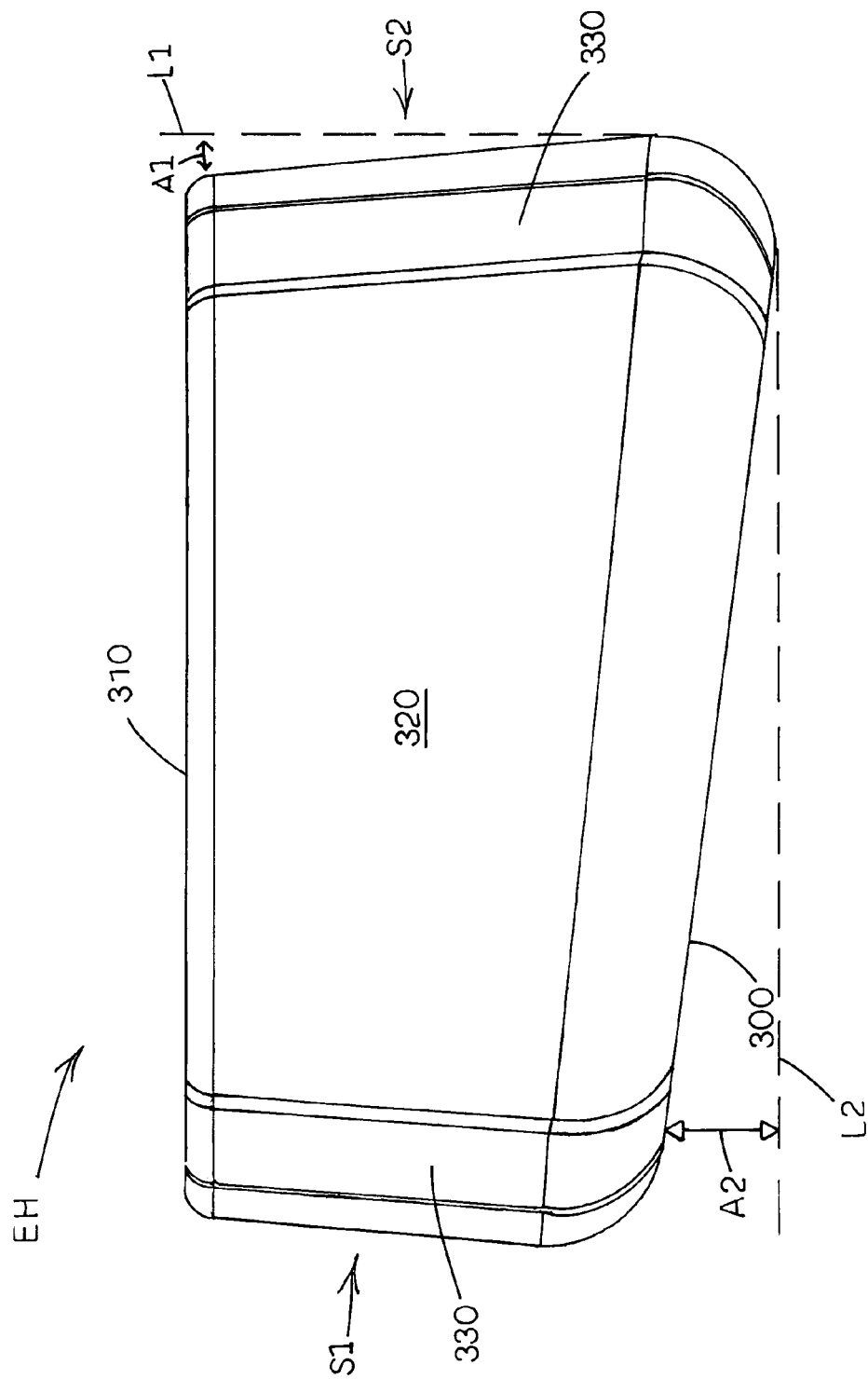
FIG. 5C of the drawings is a side elevation view of the expander hub shown in FIG. 1.

When present, lobes 330 can each extend radially past the outer diameter of expander hub EH that is defined by outer wall 320, and lobes 330 can extend from the uppermost surface 310 of expander hub EH to the lowest surface 300 of expander hub EH. As illustrated in FIGS. 5A-5D, the outer diameter of expander hub EH at uppermost surface 310 is less than the outermost diameter of expander hub EH at lowest surface 300. Outer wall 320 extends between uppermost surface 310 and lowest surface 300 wherein outer wall 320 can be aligned as illustrated in FIG. 5C at an angle A1 of from at least about 2° to 8° from a vertical line designated in phantom as line L1.

Figure 5D:
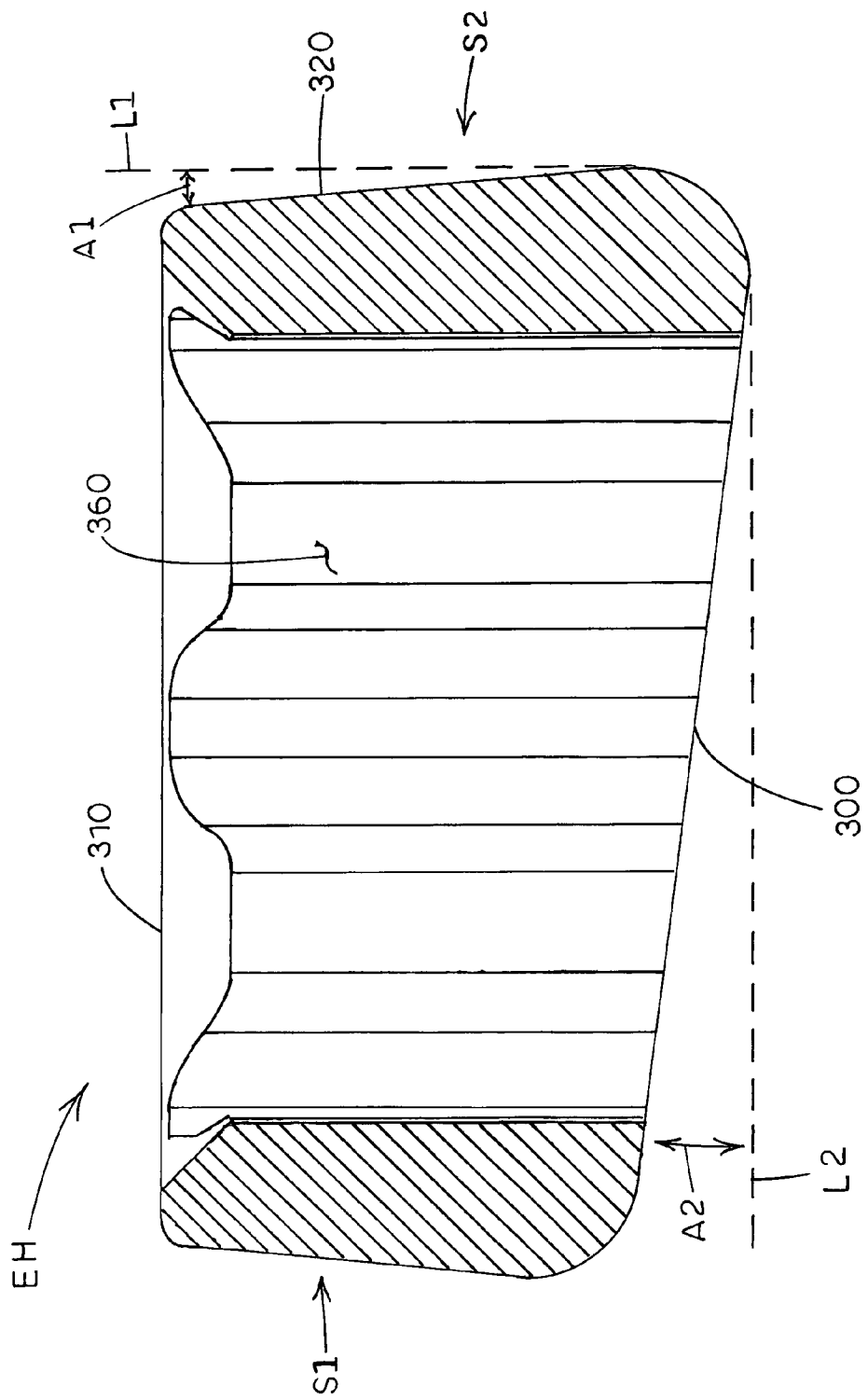
FIG. 5D of the drawings is a sectional view of the expander hub shown in FIG. 5C.

As best illustrated in FIGS. 5C and 5D of the drawings, lowest surface 300 of expander hub EH can extend along a line that is not parallel with the line along which uppermost surface 310 extends. Instead, expander hub EH can include a short side generally designated S1 and a long side generally designated S2 with uppermost surface 310 extending therebetween along a line which is at least substantially horizontal but with lowest surface 300 extending along a line therebetween which can be at an angle A2 of from about at least 6° to 12° from line L2, which is parallel to uppermost surface 310 as illustrated in FIGS. 5C and 5D.

The inner diameter of expander hub EH can be of any suitable shape designed for receiving a driver in order to rotate expander hub EH. As illustrated particularly in FIGS. 5A, 5B and partially in FIG. 5D, expander hub EH includes an inner wall 360 which defines an opening through the center of expander hub EH and which forms a shape adapted for receiving a driver for rotating driving expander hub EH. As shown, inner wall 360 forms a hexagonal recess adapted for receiving a driver with a matching hexagonal driving end for rotating expander hub EH. As can be appreciated by those of skill in the art, any suitable shape can be formed by inner wall 360 in order to suitably rotate expander hub EH. As can be appreciated further hereinafter, a driver for fitting into recess 230 of base portion 220 of head portion H can be inserted through the middle of expander hub EH in order to rotate head portion H into shank portion SP as can be appreciated by those of skill in the art. To facilitate such a feature, recess 230 of head portion H can be smaller in diametrical size as compared with the central opening defined by inner wall 360 of expander hub EH.

Figure 6:
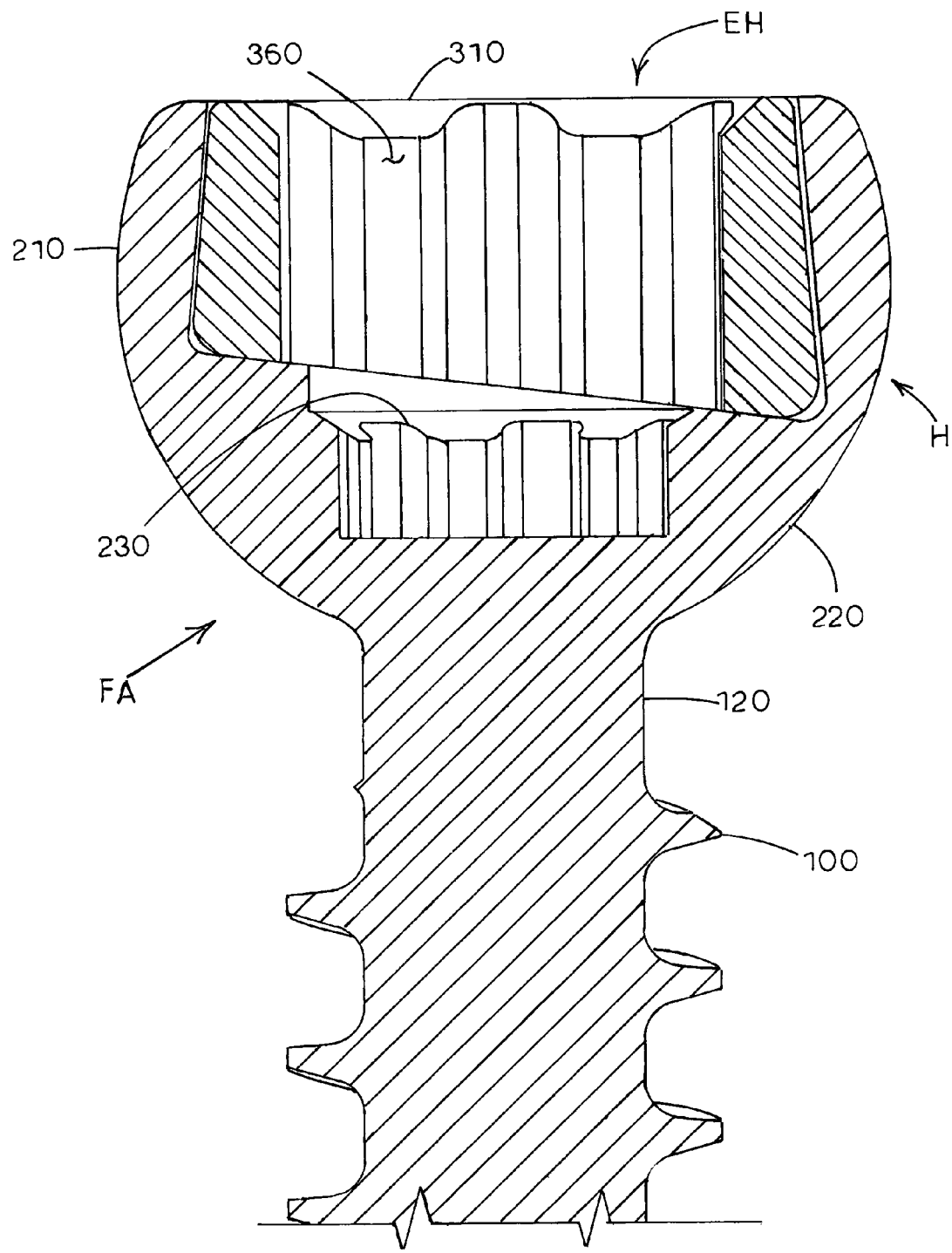
FIG. 6 of the drawings is a sectional view of an end portion of the fixation apparatus of Figure shown in FIG. 2 with the expander hub in place.

FIG. 6 illustrates expander hub EH positioned within head portion H of fixation apparatus FA. As shown, expander hub EH is in what is referred to herein as an unlocked position, wherein the lowest surface of expander hub EH is at least substantially flat against upper surface 240 of head portion H. In this position, there is little or no pressure exerted by outer wall 320 of expander hub EH against inside 260 of head portion H. As shown, uppermost surface 310 of expander hub EH is at least substantially at the level of top end 250 of head portion H of fixation apparatus FA. FIG. 7A also illustrates expander hub EH in this unlocked position providing a top, plan view of expander hub EH within head portion H of fixation apparatus FA. Although lobes 330 are considered optional and not necessary for locking of fixation apparatus FA, when present, lobes 330 of expander hub EH can be aligned with slots 220 of head portion H in the unlocked position shown in FIG. 7A. FIG. 9A illustrates fixation apparatus FA positioned through a hole 400 of a plate P with expander hub EH in this unlocked position.

From the position shown in FIGS. 6 and 7, expander hub EH can be locked in position in head portion H by simply suitably rotating expander hub EH. FIG. 7B illustrates initiation of this locking process as expander hub EH has been rotated in a clockwise direction within head portion H. Although optional, lobes 330 as shown when present in FIG. 7B move out of alignment with slots 220 and can begin to exert pressure against wall sections 210 of head portion H.

Figure 7C:
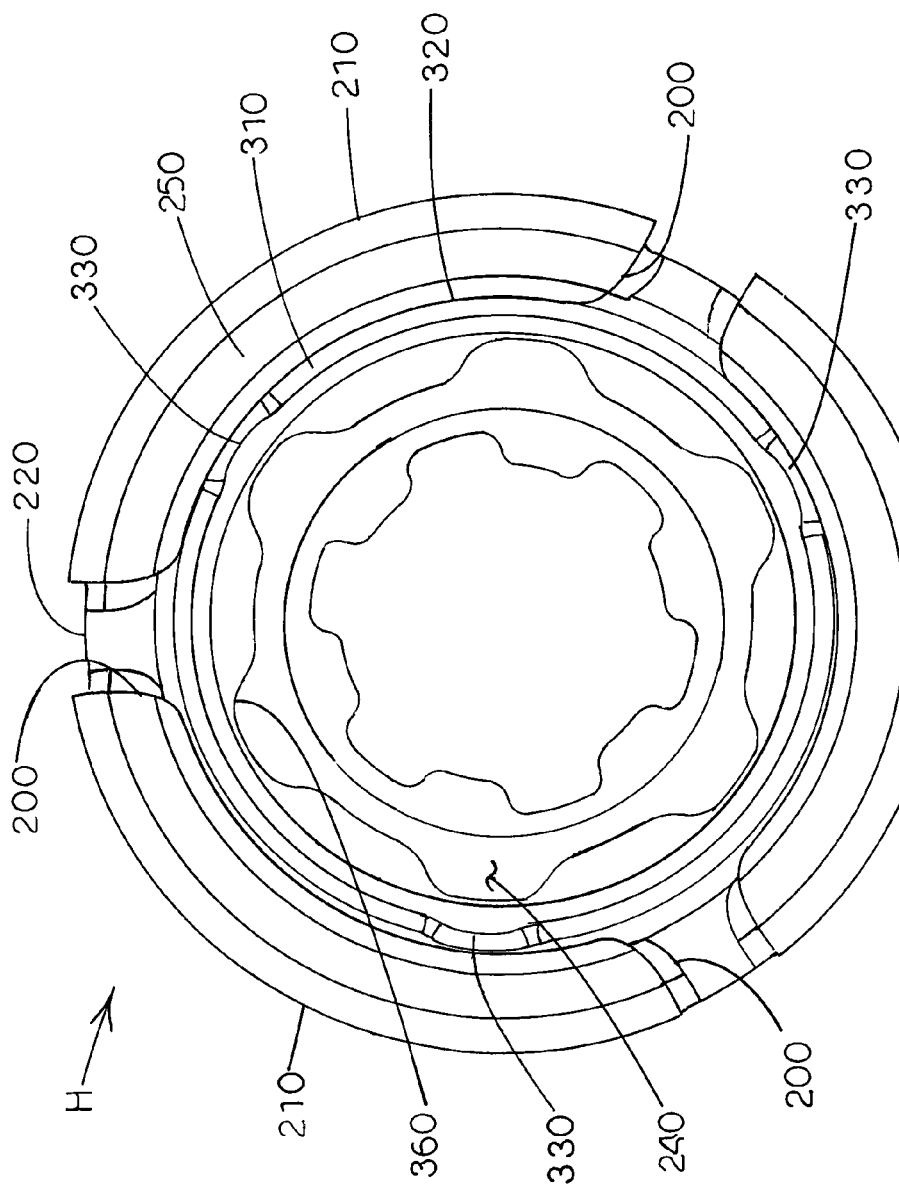

FIG. 7C illustrates expander hub EH locked in position within head portion H as expander hub EH has been rotated even further from its position shown in FIG. 7B wherein lobes 330 are further away from slots 220 and press against wall sections 210 of head portion H. As shown with the disclosed configuration, each one of wall sections 210 has one of lobes 330 exerting outward force against it. In this manner, wall sections 210 of head portion H can be forced to move outwardly sufficient to press wall sections against any structure receiving fixation apparatus FA, as further described hereinbelow.

Figure 8:
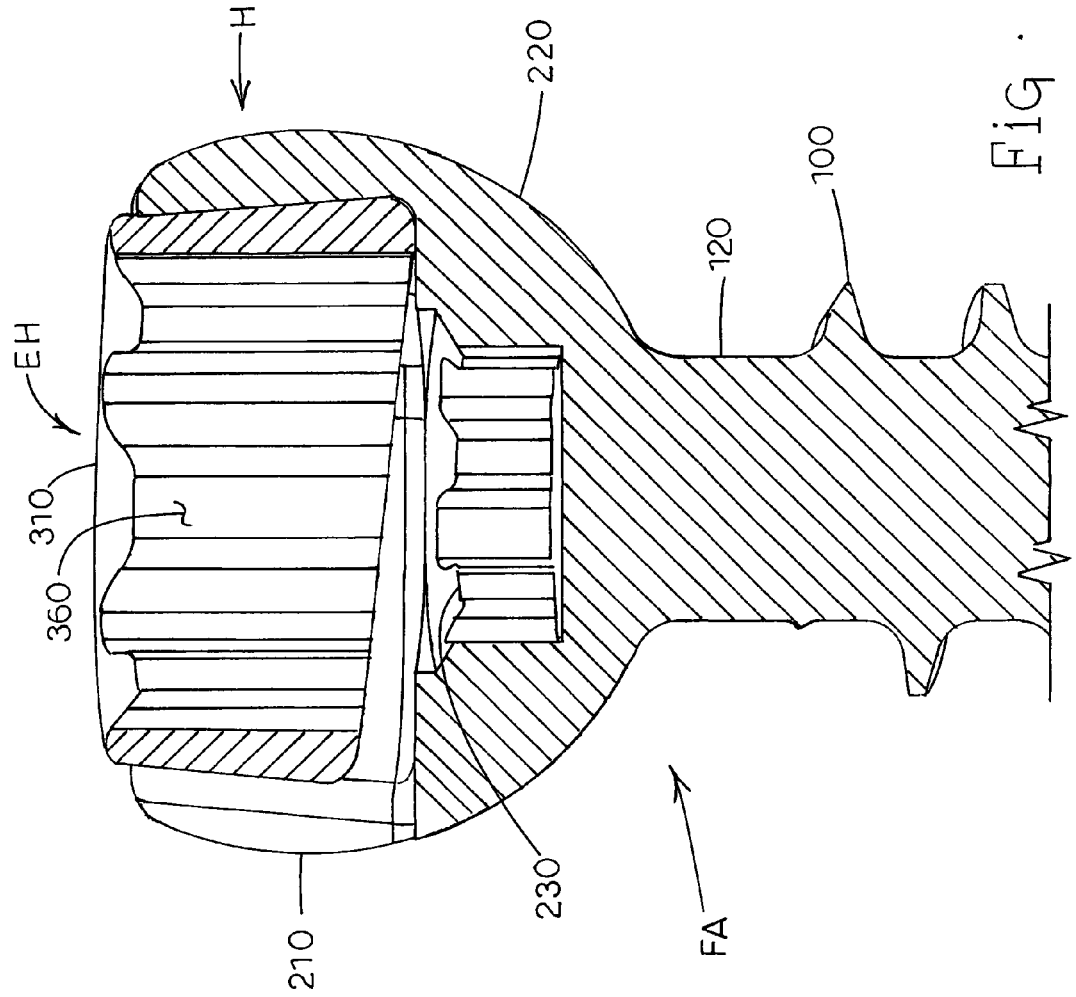
FIG. 8 of the drawings is a sectional view of and end portion of the fixation apparatus of FIG. 6 illustrating the expander hub in a locked position.

FIG. 8 of the drawings also illustrates expander hub EH in the locked position shown in FIG. 7C, but from a cross-sectional viewpoint. As shown, the rotation of expander hub EH to reach this locked position has vertically raised expander hub EH within head portion H such that uppermost surface 310 of expander hub EH is now higher than the level of top end 250 of head portion H of fixation apparatus FA. This elevation of expander hub EH results due to the incline or taper of upper surface 240 of head portion H and the incline of lowest surface 300 of expander hub EH. Since these inclined surfaces at least substantially match to allow expander hub EH to rest or fit at least like a puzzle piece against upper surface 240 of head portion H when in the unlocked position, rotation of expander hub EH to the locked position as described understandably raises expander hub EH as shown as the inclined surfaces of upper surface 240 and lowest surface 300 move away from this fitted position.

The reverse taper of inside 260 of wall sections 210 of head portion H facilitates retaining expander hub EH within head portion H as expander hub EH changes elevation relative to head portion H. The incline or taper of outer wall 320 of expander hub EH is designed for cooperation with this reverse taper feature to allow desirable movement of expander hub EH. The vertical or rising movement of expander hub EH within head portion H caused by rotation of expander hub EH causes outer wall 320 of expander hub EH, by its greater lower diameter and gradually decreasing upper diameter, to exert force on inside 260 of wall sections 210 of head portion H to force wall sections 210 outwardly, especially when inside 260 of wall sections 210 has a gradual incline or taper opposite from outer wall 320 of expander hub EH.

FIGS. 9A and 9B of the drawings show a close-up view of fixation apparatus FA positioned through hole 400 of plate P. Expander hub EH is in an unlocked position in FIG. 9A where little or no pressure is exerted by wall sections 210 of head portion H against the inner wall of hole 400 of plate P to hold or maintain fixation apparatus FA in any specific position or alignment. Expander hub EH is in its locked position in FIG. 9B where wall sections 210 of head portion H are forced outwardly by expander hub EH to exert sufficient pressure against the inner wall of hole 400 to maintain and lock fixation apparatus FA in a desired position and alignment it extends through hole 400 of plate P. Sufficient pressure can exist plate P to lock fixation apparatus FA in position where the angle at which fixation apparatus FA is positioned through and within hole 400 of plate P can also be fixed and locked.

Figure 10:
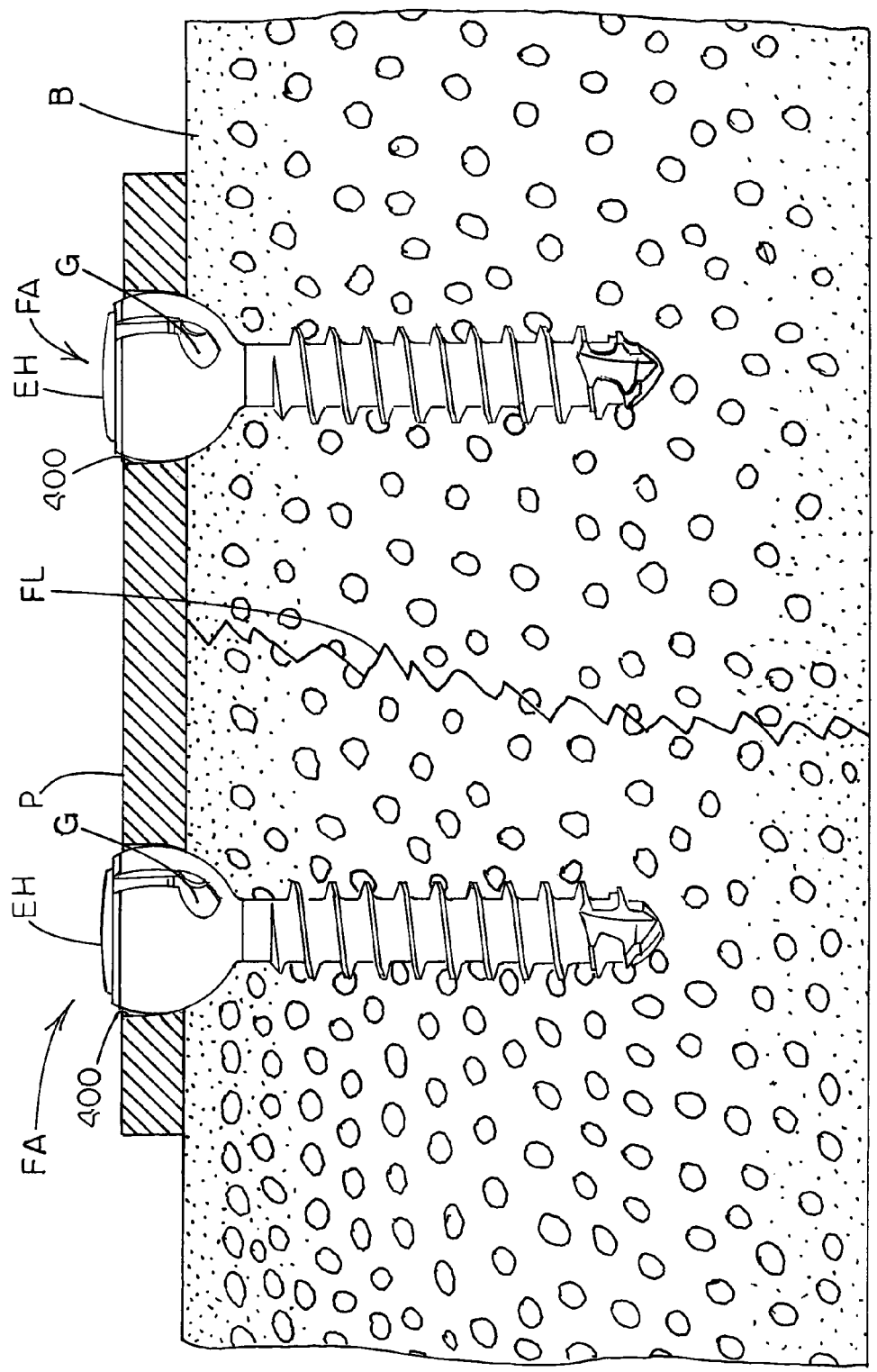
FIG. 10 of the drawings is a sectional view illustrating two fixation apparatuses locked in place against a plate to fixate a fracture.
Figure 12C:
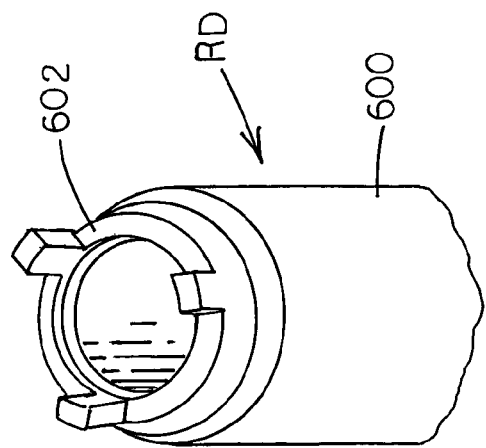
FIG. 12A-12C of the drawings are perspective views of the head portions of the drivers of FIGS. 11A, 11B and 11C, respectively.
Figure 12B:
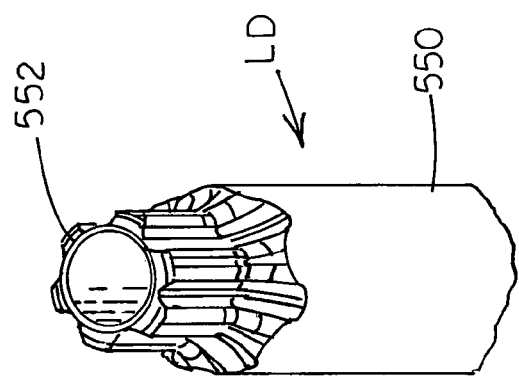
Figure 12A:
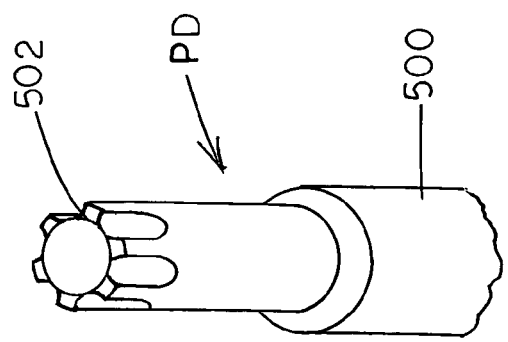

FIG. 10 illustrates, for exemplary purposes and without limitation, two identical fixation apparatuses FA extending through holes H of plate P and partially into bone B. Plate P extends across a bone fracture line FL and is held in position there to fixate fracture line FL. As can be appreciated by those of skill in the art, any suitable number of fixation apparatuses could be used with any suitable configuration of holes and plates as may be desired depending upon the situation. It is envisioned of course that one or more plates such as plate P can be utilized with one or more fixation apparatuses FA, and that fixation apparatuses FA can be locked into any suitable position or alignment to fixating a fracture. For example, fixation apparatuses FA may extend through material other than bone immediately under a hole 400, such as through soft tissue or other non-bone material. As shown in FIG. 10, groove G of each fixation apparatus FA has allowed each head portion H to self-counterbore into bone B so as to be below the upper surface of bone B.

While any suitable drivers could be used in association with the subject matter described herein, FIGS. 11A, 11B, 11C, 12A, 12B, and 12C, 13 and 14 illustrate, without limitation, exemplary embodiments of drivers that can be used. Placement driver PD is shown generally designated in FIGS. 11A, 12A, 13 and 14 and can be used to drive fixation apparatus FA into suitable material such as bone. Placement driver PD can be elongated and include a shaft portion 500 terminating in an end 502 configured to mate with recess 230 (FIGS. 3 and 4) within head portion H. As shown, end 502 comprises a hexagonal shape to at least substantially matingly engage recess 230. In this manner, rotation of placement driver PD forces likewise rotation of fixation apparatus FA. Any suitable material of construction can be used for placement driver PD, such as, for example, titanium.

Locking driver LD is shown generally designated in FIGS. 11B, 12B, 13 and 14 and can be used to lock expander hub EH. Locking driver LD can be elongated and cannulated to fit over at least a portion of placement driver PD as further described hereinbelow. Locking driver LD preferably includes a shaft 550 and terminates in one end 552 which is configured to be inserted into the middle of expander hub EH to matingly engage inner wall 360. In this manner, rotation of locking driver LD forces likewise rotation of expander hub EH. Any suitable material of construction can be used for locking driver LD, such as, for example, titanium.

When shank portion SP is connected to head portion H, rescue driver RD is shown generally designated in FIGS. 11C, 12C, 13 and 14 and can be used to stop rotation of head portion H. This function of rescue driver RD is not necessary when shank portion SP is part of or connected with head portion H. Rescue driver RD can be elongated and cannulated to fit over at least a portion of locking driver LD as further described hereinbelow. Rescue driver RD preferably includes a shaft 600 terminating in an end which can include tabs 602. Rescue driver RD can be configured to be inserted into slots 200 of head portion H. In this manner, rotation of rescue driver RD limits rotation of head portion H during locking. A handle 604 can be attached to the end of rescue driver RD opposite end 602 and used for gripping to apply rotational force to rescue driver RD. Any suitable material of construction can be used for rescue driver RD, such as, for example, titanium.

Figure 13:
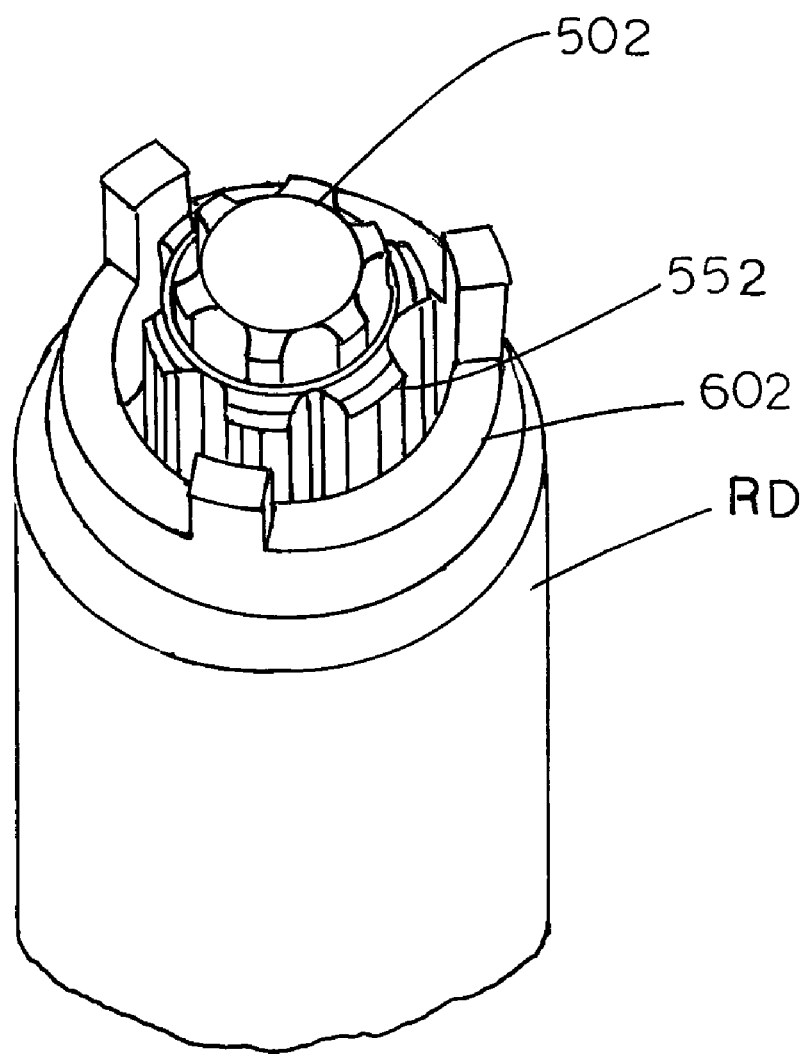
FIG. 13 of the drawings is a perspective view of the drivers of FIGS. 11A-11C and 12A-12C assembled together for use.
Figure 14:
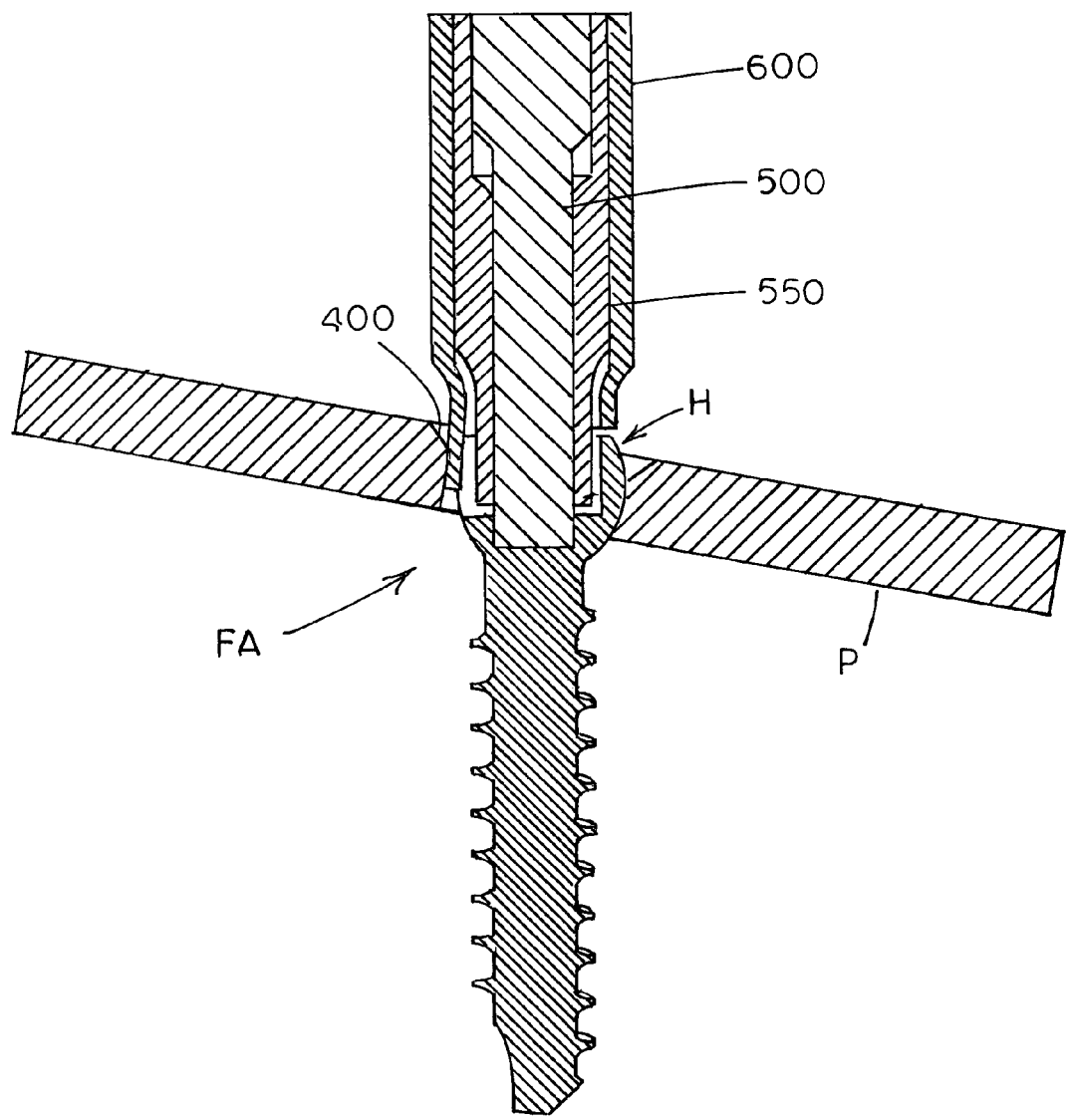
FIG. 14 of the drawings is a sectional view of the assembly of drivers of FIG. 13 positioned against the fixation apparatus for use.

FIG. 13 illustrates a nested and concentric configuration for the drivers shown in FIGS. 11A-12C, and FIG. 14 illustrates the nested configuration of drivers in contact with fixation apparatus FA which extends through hole 400 of plate P. Placement driver PD is shown at the center, with locking driver LD positioned over or around placement driver PD, but with end 500 of placement driver PD extending farther that end 550 of locking driver LD. Rescue driver RD is positioned over or around locking driver LD as shown. From this configuration, and as can be readily appreciated by those of skill in the art, the drivers can be used in cooperation with one another without having to remove each before using another.

Exemplary Method of Use

It is envisioned that a fixation apparatus FA with the expander hub as disclosed herein could be used in any manner known to those of skill in the art based upon the present disclosure. When utilized for fixating a bone fracture, as a non-limiting example, a surgeon can be presented with any suitable plate, such as plate P (such as shown in FIGS. 9A, 9B, 10 and 14) for affixing across a bone fracture and a screw. Plate P can be provided with any suitable configuration of holes defined therethrough, such as hole 400 for receiving fixation apparatus FA. The shape and size of hole 400 can be of any suitable shape and size, such as spherical, as can be appreciated by those of skill in the art. Expander hub EH can be positioned (without being locked) in head portion H of fixation apparatus FA prior to packaging.

Plate P can be placed over an appropriate bone site, such as above and/or across a fracture line FL, as shown for example in FIG. 10, using any suitable driver, such as placement driver PD shown in FIGS. 11A, 12A, 13 and 14. By applying rotational pressure to placement driver PD, fixation apparatus FA can be driven into bone. As head portion H of fixation apparatus FA passes through the entrance to hole 400 in plate P, the smaller outer diameter of expander hub EH, and, when present, lobes 330 resting within slots 200 of fixation apparatus FA, allow slots 200 to narrow, and the outer diameter of fixation apparatus FA to compress and slide through the opening of hole 400. Fixation apparatus FA can continue to be driven by placement driver PD until sufficient "lag" compression is obtained between plate P and head portion H of fixation apparatus FA. At this point, fixation apparatus FA can rotate relative to plate P about the center of hole 400.

Once fixation apparatus FA is positioned and suitably driven into bone B through hole 400 by placement driver PD, locking driver LD can be used, without removing placement driver PD so as to hold fixation apparatus FA stationary, to rotate expander hub EH within head portion H of fixation apparatus FA to lock expander hub EH and thereby lock in place fixation apparatus FA. For this "locking" to occur, first lobes 330, when present, of head portion H engage, with interference, inside 260 of wall sections 210 of head portion H. The rotation also causes the inclination of upper surface 240 within head portion H and that of lowest surface 300 of expander hub EH to force expander hub EH to elevationally and axially move upward within head portion H of fixation apparatus FA. This movement engages the tapered surface of outer wall 320 of expander hub EH and that of inside 260 of wall sections 210 of head portion H further creating a radial, outward pressure on inside 260 of wall sections 210 of head portion H. The outer diameter of fixation apparatus FA is thereby expanded, interfering with the inner diameter of the hole, such as hole 400, of plate P, and creating friction, which locks the angle and alignment of fixation apparatus FA in place through hole 400. Fixation apparatus FA can advantageously be used with P plate whereby fixation apparatus FA and plate P can compress bone separately from locking the fixation apparatus in a desired position. Also, the angle, alignment or position of fixation apparatus FA can be changed if desired even after locking of fixation apparatus FA.

It can therefore be seen that the angle and alignment of the fixation apparatus can be adjusted after placement of fixation apparatus FA, but prior to locking. This advantageously allows the position of fixation apparatus FA to be aligned using the angle of fixation apparatus FA, and advantageously allows fixation apparatus FA to be held in place with the locking aspect as described. Locking of fixation apparatus FA is optional and is not a necessary step for fixating a bone fracture. By nature of the design, expander hub EH cannot come free from the head portion of fixation apparatus FA, thus avoiding the potential introduction of a free foreign body under the skin. Even if expander hub EH were to become unlocked or disengaged after locking, the system as disclosed herein would continue to function as well as conventional bone fixation systems. With fixation apparatus FA locked in place as described herein, three potential undesirable failures of conventional fixation apparatus systems that are avoided include torsional back-out, change of the angle of the fixation apparatus, and pull-out of the fixation apparatus.

It will be understood that various details of the subject matter disclosed herein may be changed without departing from the scope of the subject matter. Furthermore, the foregoing description is for the purpose of illustration only, and not for the purpose of limitation.

That which is claimed:

1. A fixation apparatus for use in fixating bone, the fixation apparatus comprising:
    (a) a head portion comprising a plurality of outer wall sections at least partially surrounding a central hollow area with the outer wall sections having inner sides facing the central hollow area, the head portion having an inner bottom surface and a top end with the inner bottom surface disposed between the inner sides, and the top end of the head portion defining an opening between the outer wall sections with the inner sides of the outer wall sections tapered inwardly toward the central hollow area from the inner bottom surface to the top end;
    (b) an expander hub adapted for positioning at least partially within the central hollow area and seated at least partially on the inner bottom surface of the head portion; and
    (c) the expander hub being rotatable upwardly from the inner bottom surface toward the opening at the top end of the head portion to force at least one of the outer wall sections of the head portion outwardly to lock the fixation apparatus in a desired position.

2. The fixation apparatus according to claim 1 further comprising a shank portion extending from the head portion.

3. The fixation apparatus according to claim 2 wherein the shank portion is integral and formed as an extension of the head portion.

4. The fixation apparatus according to claim 2 wherein the shank portion is separate from and extends from the head portion.

5. The fixation apparatus according to claim 2 wherein the shank portion is threaded.

6. The fixation apparatus according to claim 2 wherein the shank portion is non-threaded.

7. The fixation apparatus according to claim 1 wherein the head portion is self-counterboring.

8. The fixation apparatus according to claim 1 wherein the wall sections of the head portion comprise a plurality of wall sections extending from a portion of the fixation apparatus, the wall sections defining slots between each wall section which provide a space between adjacent wall sections.

9. The fixation apparatus according to claim 8 wherein the slots are at least substantially parallel to one another.

10. The fixation apparatus according to claim 9 further comprising a shank portion extending from the head portion and wherein the slots of the head portion extend in a direction at least substantially parallel to an axis along which the shank portion extends.

11. The fixation apparatus according to claim 1 wherein the head portion is at least substantially spherical.

12. The fixation apparatus according to claim 1 wherein the inner bottom surface of the head portion defines a recessed opening.

13. The fixation apparatus according to claim 1 wherein the inner bottom surface of the head portion comprises an at least a partially inclined bottom surface.

14. The fixation apparatus according to claim 13 wherein the expander hub has a bottom surface that is at least partially inclined.

15. The fixation apparatus according to claim 1 wherein the expander hub is at least generally cylindrical.

16. The fixation apparatus according to claim 15 wherein the expander hub comprises an inclined bottom surface.

17. The fixation apparatus according to claim 1 wherein the expander hub comprises a plurality of lobes on an outer surface of the expander hub.

18. The fixation apparatus according to claim 17 wherein the lobes on the expander hub extend outwardly.

19. The fixation apparatus according to claim 1 wherein the expander hub comprises a plurality of annular recesses for receiving a driver for rotating the expander hub.

20. The fixation apparatus according to claim 1 wherein the expander hub is at least generally cylindrical in shape and has a reverse tapered outer diameter such that an outer diameter of the expander hub is greater at its bottom surface than an outer diameter of the expander hub at its uppermost surface.

21. A fixation apparatus for use in fixating bone, the fixation apparatus comprising:
(a) a head portion comprising a plurality of outer wall sections at least partially surrounding a central hollow area with the outer wall sections having inner sides facing the central hollow area, the head portion having an inner bottom surface and a top end with the inner bottom surface disposed between the inner sides, and the top end of the head portion defining an opening between the outer wall sections with the inner sides of the outer wall sections tapered inwardly toward the central hollow area from the inner bottom surface to the top end;
(b) an expander hub positioned at least partially within the head portion and seated at least partially on the inner bottom surface of the head portion with the outer wall sections of the head portion at least partially surrounding the expander hub; and
(c) the expander hub being rotatable upwardly from the inner bottom surface and toward the opening at the top end of the head portion to force at least one of the outer wall sections of the head portion outwardly to lock the fixation apparatus in a desired position.

22. The fixation apparatus according to claim 21 further comprising a shank portion extending from the head portion.

23. The fixation apparatus according to claim 22 wherein the shank portion is integral and formed as an extension of the head portion.

24. The fixation apparatus according to claim 22 wherein the shank portion is separate from and extends from the head portion.

25. The fixation apparatus according to claim 22 wherein the shank portion is threaded.

26. The fixation apparatus according to claim 22 wherein the shank portion is non-threaded.

27. The fixation apparatus according to claim 21 wherein the head portion is self-counterboring.

28. The fixation apparatus according to claim 21 wherein the wall sections of the head portion comprise a plurality of wall sections extending from a portion of the fixation apparatus, the wall sections defining slots between each wall section which provide a space between adjacent wall sections.

29. The fixation apparatus according to claim 21 wherein the head portion is at least substantially spherical.

30. The fixation apparatus according to claim 29 wherein the slots are at least substantially parallel to one another.

31. The fixation apparatus according to claim 30 further comprising a shank portion extending from the head portion and wherein the slots extend in a direction at least substantially parallel to an axis along which the shank portion extends.

32. The fixation apparatus according to claim 21 wherein the inner bottom surface of the head portion defines a recessed opening.

33. The fixation apparatus according to claim 21 wherein the inner bottom surface of the head portion comprises an at least a partially inclined bottom surface.

34. The fixation apparatus according to claim 33 wherein the expander hub has a bottom surface that is at least a partially inclined.

35. The fixation apparatus according to claim 21 wherein the expander hub is at least generally cylindrical.

36. The fixation apparatus according to claim 35 wherein the expander hub comprises an inclined bottom surface.

37. The fixation apparatus according to claim 21 wherein the expander hub comprises a plurality of lobes on an outer surface of the expander hub.

38. The fixation apparatus according to claim 37 wherein the lobes on the expander hub extend outwardly.

39. The fixation apparatus according to claim 21 wherein the expander hub comprises a plurality of annular recesses for receiving a driver for rotating the expander hub.

40. The fixation apparatus according to claim 21 wherein the expander hub is at least generally cylindrical in shape and has a reverse tapered outer diameter such that an outer diameter of the expander hub is greater at its bottom surface than an outer diameter of the expander hub at its uppermost surface.

* * * * *